(12) United States Patent
Lubisch et al.

(10) Patent No.: US 6,251,917 B1
(45) Date of Patent: Jun. 26, 2001

(54) BENZAMIDOALDEHYDES AND THEIR USE AS CYSTEINE PROTEASE INHIBITORS

(75) Inventors: Wilfried Lubisch, Mannheim; Achim Möller, Grünstadt; Hans-Jörg Treiber, Brühl, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/297,916

(22) PCT Filed: Nov. 11, 1997

(86) PCT No.: PCT/EP97/06292

§ 371 Date: May 12, 1999

§ 102(e) Date: May 12, 1999

(87) PCT Pub. No.: WO93/23581

PCT Pub. Date: Apr. 6, 1998

(30) Foreign Application Priority Data

Nov. 26, 1996 (DE) ................................ 196 48 793

(51) Int. Cl.⁷ .......................... A61K 31/47; A61K 31/18; A61K 31/166; C07D 215/36; C07C 237/42; C07C 311/114

(52) U.S. Cl. ................ 514/311; 514/312; 514/345; 514/347; 514/355; 514/357; 514/617; 514/618; 514/619; 514/620; 514/621; 514/622; 546/153; 546/157; 546/172; 546/293; 546/314; 546/316; 546/337; 564/161; 564/162; 564/164; 564/166; 564/168; 564/169; 564/180; 564/181

(58) Field of Search ................ 514/311, 312, 514/345, 347, 355, 357, 617, 618, 619, 620, 621, 622; 546/153, 157, 172, 293, 314, 316, 337; 564/161, 162, 164, 166, 168, 169, 180, 181

(56) References Cited

U.S. PATENT DOCUMENTS 5,858,982 * 1/1999 Tung ........................ 514/19

FOREIGN PATENT DOCUMENTS

| 363 284 | 4/1990 | (EP) . |
| 520 336 | 12/1992 | (EP) . |
| 611 756 | 8/1994 | (EP) . |
| 92/12140 | 7/1992 | (WO) . |
| 93/14082 | 7/1993 | (WO) . |
| 95/09838 | 4/1995 | (WO) . |
| 96/39194 | 12/1996 | (WO) . |

OTHER PUBLICATIONS

Int. J. Bio. vol. 23, No. 9, 819–821, (1991), Mondola et al.
Bio. Chem. vol. 376, No. 1, Jan. 1995, Suzuki et al. 523–529 (1995).
Life Sci., vol. 48, 1659–1669, Barrett et al. (1991).
Calpain Inhibition, Wang et al., Tips, Nov. 94, vol. 15 (1994).
Neuroprotection with a Calpain Inhibitor . . . Hong et al., Stroke, vol. 25, No. 3, Mar. (1994).
Jp. 08 183 759—Abstract (1996).
Synthesis, Feb. 1994, 181–184, Attanasi et al. (1994).
J. Cerebral Blood Flow.. 14:537, (1994), Bartus et al., 537–544.
Int. J. Methods in Synthetic Org. Chem, No. 8, Aug. (1983), 605–684.
Neurological Res., (1995), vol. 17, Aug., 249–258.
Proc. Natl. Acad. Sci., vol. 93, 3428–3433, Apr. (1996), Saatman et al.
Proc. Natl. Acad. Sci, vol. 92, 7662–7666, Aug., (1995) Edelstein et al.
Jp. Cir. J., vol. 59, Jan. (1995), Yoshida et al., 40–48.
Neuron, vol. 14, 651–659, Mar. (1995), Higaki et al.
Cytokine, vol. 6, No. 6, Nov. (1994) 597–601, Watanabe et al.
Int. J. of Oncology 5, Supp. (1994) Takahashi et al.
Biochemical and Biophysical Research Comm., 432–435, vol. 158, No. 2, (1989), McGowan et al.
J. of Med. Chem. Jan. 24, 1992, vol. 35 No. 2,216–220, (1990) Angliker et al.
Cgen, Kettersm 191–194, (1990), Chem. Soc. of Japan, Matsueda et al.
Trends in Biochemical Sci. vol. 16, (1991), Mehdi.

* cited by examiner

*Primary Examiner*—Evelyn Mei Huang
(74) *Attorney, Agent, or Firm*—Keil & Weinkauf

(57) ABSTRACT

Compounds of the formula

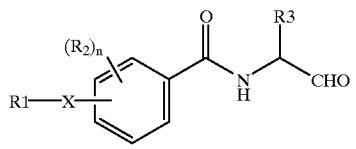

I where $R^1$, $R^2$, $R^3$, X and n are as defined in the description, are inhibitors of cysteine protease.

14 Claims, No Drawings

BENZAMIDOALDEHYDES AND THEIR USE AS CYSTEINE PROTEASE INHIBITORS

This application is the national phase of PCT/EP97/06292, filed Nov. 11, 1997.

The present invention relates to novel benzamidoaldehydes and to their application for controlling disorders.

Calpains are intracellular proteolytic enzymes of the group of the cysteine proteases and are found in many cells. Calpains are activated by elevated calcium concentrations, a distinction being made between calpain I or micro-calpain, which is activated by micro-molar concentrations of calcium ions, and calpain II or m-calpain, which is activated by m-molar concentrations of calcium ions (P. Johnson, Int.J-.Biochem. 22(8) 1990, 811–22). Further calpain isoenzymes are now being postulated (K. Suzuki et al., Biol.Chem. Hoppe-Seyler, 376(9) (1995), 523–9).

Calpains are thought to play an important role in various physiological processes. These include: the cleavage of regulatory proteins—such as protein kinase C, cytoskeletal proteins (such as MAP 2 and spectrin), muscular proteins, proteins involved in the activation of platelets, proteins involved in mitosis and others which are listed in M. J. Barrett et al., Life Sci. 48 (1991), 1659–69 and K. K. Wang et al., Trends in Pharmacol.Sci., 15 (1994), 412–9; protein breakdown in rheumatoid arthritis and neuropeptide metabolism.

Elevated calpain levels were detected in various pathophysiological processes, for example, ischemia of the heart (for example myocardial infarction), the kidney or the central nervous system (for example stroke), inflammations, muscular dystrophies, cataracts of the eyes, injuries of the central nervous system (for example trauma) and Alzheimer's disease (see K. K. Wang, above). It is therefore assumed that these disorders are linked to increased intracellular calcium levels. Owing to this, calcium-dependent processes are overactivated and no longer subject to physiological regulation. Accordingly, an overactivation of calpains can also cause pathophysiological processes.

It has therefore been postulated that inhibitors of calpain enzymes may be useful for the treatment of these disorders. This has been confirmed by various studies. Thus, Seung-Chyul Hong et al., Stroke 25 (3) (1994), 663–9 and R. T. Bartus et al., Neurological Res. 17 (1995), 249–58, demonstrated a neuroprotective action of calpain inhibitors in acute neurodegenerative disorders or ischemia, such as occur after a stroke. After experimental brain trauma, calpain inhibitors improved the deficits of memory performance and the neuromotoric disorders that occurred (K. E. Saatman et al. Proc.Natl.Acad.Sci. USA, 93, (1996), 3428–3433). C. L. Edelstein et al., Proc.Natl.Acad.Sci. USA, 92 (1995), 7662–6, observed a protective activity of calpain inhibitors in kidneys damaged by hypoxia. Yoshida, Ken Ischi et al., Jap.Circ.J. 59(1) (1995), 40–8, were able to demonstrate favorable effects of calpain inhibitors after cardial damage brought about by ischemia or reperfusion. Since calpain inhibitors inhibit the release of the β-AP4 protein, a potential application as therapeutic agent for Alzheimer's disease has been suggested (J. Higaki et al., Neuron, 14 (1995), 651–59). The release of interleukin-1α is also inhibited by calpain inhibitors (N. Watanabe et al., Cytokine 6(6) (1994), 597–601). It has furthermore been demonstrated that calpain inhibitors exhibit cytotoxic effects in tumor cells (E. Shiba et al. 20th Meeting Int.Ass.Breast Cancer Res., Sendai Jp, Sep. 25–28, 1994, Int.J.Oncol. 5(Suppl.), (1994), 381).

Further possible applications of calpain inhibitors are listed in K. K. Wang, Trends in Pharmacol.Sci., 15 (1994), 412–8.

Calpain inhibitors have already been described in the literature. However, they are predominantly either irreversible or peptidic inhibitors. Irreversible inhibitors are usually alkylating substances, which have the disadvantage that they react nonselectively in the organism or that they are instable. For this reason, these inhibitors often exhibit undesirable side-effects, such as toxicity, and their applications are therefore limited, or they are not useful. The irreversible inhibitors include, for example, the epoxides E 64 (E. B. McGowan et al., Biochem.Biophys.Res.Commun. 158 (1989), 432–5), α-haloketones (H. Angliker et al., J.Med-.Chem. (1992), 216–20) and disulfides (R. Matsueda et al., Chem.Lett. (1990), 191–194).

Many known reversible inhibitors of cysteine proteases, such as calpain, are peptidic aldehydes or ketones, in particular dipeptidic and tripeptidic aldehydes, such as, for example, Z-Val-Phe-H (MDL 28170) (S. Mehdi, Trends in Biol.Sci. 16 (1991), 150–3) and the compounds of EP 520336. Under physiological conditions, peptidic aldehydes for example often have the disadvantages that they are unstable owing to the reactivity present (J. A. Fehrentz and B. Castro, Synthesis, 19983 [sic], 676–678), that they can be metabolized quickly, that they have low water-solubility (important for intravenous application) or that they are slow to cross cell membranes, such as the blood-brain barrier and cellular membranes of neurons (calpain is an intracellular enzyme and any inhibitor has to penetrate into the cells). Thus, the best known peptidic inhibitors MDL 28170, AK 275 and AK 295 (Seung-Chuyl Hong et al., Stroke 25(3) (1994), 663–669; R. T. Bartus et al., J.Cerebral Blood Flow and Metabolism, 14 (1994), 537–544) have been studied pharmacologically in animals, but effects were only observed when the substances were applied in a manner which is unconventional for treatment, for example intracerebroventricularly or intra-arterially. The use of the known calpain-inhibiting peptidic aldehydes or ketones in the treatment of disorders is therefore limited or not advantageous.

Furthermore, efforts are being made to develop reversible non-peptidic calpain inhibitors. Thus, JP 8183759, JP 8183769, JP 8183771 and EP 520336 describe aldehydes derived from dipeptides where saturated carbocyclic rings, for example cyclohexanes, or saturated heterocyclic rings, for example piperidines, were incorporated into these peptidic inhibitors replacing an amino acid, affording novel calpain inhibitors.

Furthermore, compounds have also been described which are derived from the structure

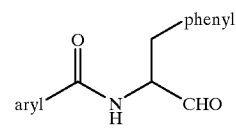

in particular compounds where aryl is a phenyl ring which may carry simple substituents such as alkyl radicals (WO 95/09838; WO 93/14082; WO/12140; Synthesis 181 (1995); EP 363284; J 59206-344 and DT 2050679). However, as shown in Synthesis 181 (1995), compounds where aryl= phenyl are only weak inhibitors of the enzyme calpain. It is not known whether substituents on this phenyl ring influence the inhibitory activity of the compounds.

It is an object of the present invention to provide non-peptidic benzamidoaldehydes having an improved activity.

We have found that this object is achieved by benzamidoaldehydes of the formula I

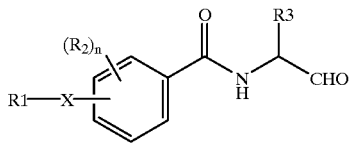

and their tautomeric and isomeric forms and, if appropriate, their physiologically acceptable salts, where:

$R^1$ is phenyl, naphthalene, quinoline, isoquinoline, tetrahydroquinoline, tetrahydroisoquinoline, pyridine, pyrimidine, pyrazine, pyridazine, quinazoline, quinoxaline, thiophene, benzothiophene, benzofuran, furan or indole, where the aromatic and heteroaromatic rings may be substituted by up to three radicals $R^4$, $R^2$ is hydrogen, chlorine, bromine, fluorine, phenyl with or without substitution by a $C_1$–$C_4$-hydrocarbon radical, —NHCO-$C_1$–$C_4$-alkyl, —NHCOPh, —NHCO-naphthyl, —NHSO$_2$-$C_{1-4}$-alkyl, CONH$_2$, COOH, —COO-$C_{1-4}$-alkyl, —O-$C_{1-4}$-alkyl, —CO—NH-$C_{1-4}$-alkyl, NO$_2$ or NH$_2$, $R^3$ is a $C_1$–$C_6$-hydrocarbon radical, which may also carry a cyclopropyl, cyclobutyl, cyclopentyl, cyclohexyl, cycloheptyl, indolyl, phenyl, pyridine or naphthyl ring, it being possible for the rings in turn to be substituted by one or two radicals $R^4$, or is an —SCH$_3$ radical, $R^4$ is $C_1$–$C_4$-alkyl, —O-$C_1$–$C_4$-alkyl, OH, Cl, F, Br, I, CF$_3$, NO$_2$, NH$_2$, CN, COOH, COO-$C_1$–$C_4$-alkyl, —NHCO-$C_1$–$C_4$-alkyl, —NHCOPh, —NHSO$_2$-$C_1$–$C_4$-alkyl, —NHSO$_2$-Ph, —(CH$_2$)$_n$—NR$^5$R$^6$ ($R^5$ and $R^6$ are identical or different and are each hydrogen, $C_{1-4}$-alkyl or together are a ring), —SO$_2$-$C_1$–$C_4$-alkyl or —SO$_2$Ph, X is a bond, —(CH$_2$)$_m$—, —(CH$_2$)$_m$—O—(CH$_2$)$_o$—, (CH$_2$)$_m$—S—(CH$_2$)$_o$—, —(CH$_2$)$_m$—SO—(CH$_2$)$_o$—, (CH$_2$)$_m$—SO$_2$—(CH$_2$)$_o$—, —CH=CH—, —C≡C—, —CO—CH=CH—, —CH=CH—CO-, —(CH$_2$)$_m$—CO—(CH$_2$)$_o$—, —(CH$_2$)$_m$—NR$^5$CO—(CH$_2$)$_o$—, —(CH$_2$)$_m$—CONR$^5$—(CH$_2$)$_o$—, —(CH$_2$)$_m$—NHSO$_2$—(CH$_2$)$_o$—, —(CH$_2$)$_m$—SO$_2$NH—(CH$_2$)$_o$—, —NH—CO—CH=CH—, —CH=CH—CO—NH— or phenyl with or without substitution by a radical $R^2$, n is the number 1 or 2, m is the number 0, 1, 2, 3 or 4 and o is the number 0, 1, 2, 3 or 4.

The compounds of the formula I can be employed as racemates or as enantiomerically pure compounds or as diastereomers. If enantiomerically pure compounds are desired, these can be obtained for example by carrying out a classical racemate resolution of the compounds of the formula I or intermediates thereof using a suitable optically active base or acid. Alternatively, the enantiomeric compounds can also be prepared by using commercially available compounds, for example optically active amino acids.

The invention also provides compounds which are mesomeric or tautomeric to compounds of the formula I, for example those compounds where the keto group of the formula I is present as the enol tautomer.

Some of the novel compounds I may contain a basic or acidic group. In these instances, compounds may exist in the form of their physiologically acceptable salts, which may be obtained by reacting the compounds with a suitable acid or base.

Suitable acids are, for example, hydrochloric acid, citric acid, tartaric acid, lactic acid, phosphoric acid, acetic acid, formic acid, maleic acid, fumaric acid, malic acid, succinic acid, malonic acid, sulfuric acid, methanesulfonic acid and toluenesulfonic acid.

Suitable bases are, in particular, sodium hydroxide, potassium hydroxide, ammonia and simple organic amines.

Preference is given to benzamidoaldehydes of the formula I where $R^2$ is hydrogen, $C_1$–$C_4$-alkyl, fluorine, chlorine or bromine, $R^3$ is CH$_2$-phenyl, which may be substituted by $R^4$, and $R^1$, X, n, m, and o are each as defined above.

The benzamidoaldehydes I according to the invention can be prepared by various routes which are outlined in the synthesis scheme below.

Synthesis scheme

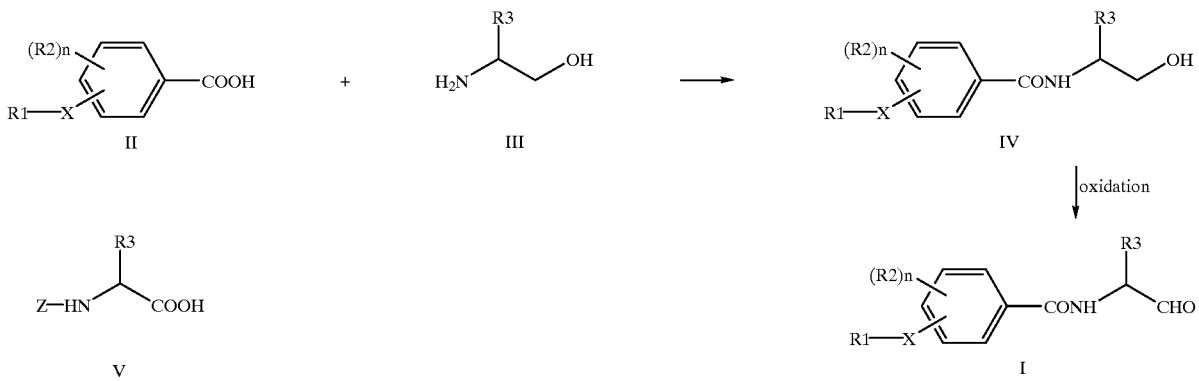

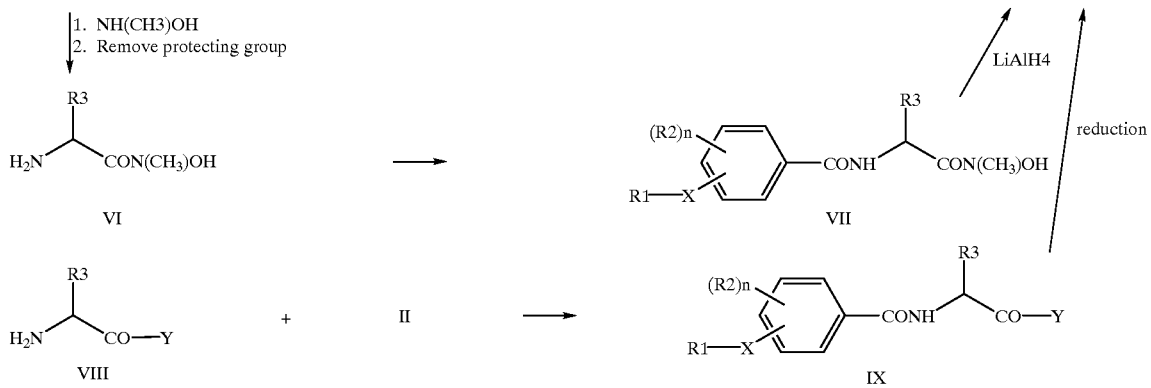

The benzoic acid derivatives II are linked with suitable aminoalcohols III to give the corresponding benzamidoaldehydes IV. For this purpose, conventional peptide coupling methods are used, such as listed for example in C. R. Larock, Comprehensive Organic Transformations, VCH Publisher, 1989, page 972f. or in Houben-Weyl, Methoden der organischen Chemie, 4th edition, E5, Chapter V. Preference is given to using "activated" acid derivatives of II where the acid group COOH is converted into a group COL. L is a leaving group, such as, for example, Cl, imidazole and N-hydroxybenzotriazole. This activated acid is then reacted with amines to give the amides IV. The reaction is carried out in anhydrous inert solvents such as methylene chloride, tetrahydrofuran and dimethylformamide at from −20 to +25° C.

These alcohol derivatives IV may be oxidized to the aldehyde derivatives I according to the invention using various conventional oxidation reactions (see C. R. Larock, Comprehensive Organic Transformations, VCH Publisher, 1989, page 604 f.) such as, for example, Swern and Swern-like oxidations (T. T. Tidwell, Synthesis 1990, 857–70), sodium hypochlorite/TEMPO (S. L. Harbenson et al., see above) or the Dess-Martin reagent (J.Org.Chem. 48 (1983), 4155). The reactions are preferably carried out in inert aprotic solvents, such as dimethylformamide, tetrahydrofuran or methylene chloride, using oxidizing agents, such as DMSO/pyridine x $SO_3$ or DMSO/oxalyl chloride, at from −50 to +25° C., depending on the method used (see literature above).

Alternatively, the benzoic acid II can be reacted with aminohydroxamic acid derivatives VI to give the benzamidoaldehydes I. For this purpose, the same reaction procedure as for the preparation of IV is used. The hydroxam derivatives VI are obtainable from the protected amino acids V by reaction with a hydroxylamine. As before, the amide preparation processes already described are employed here. The protecting group, for example Boc, is cleaved in a conventional manner, for example using trifluoroacetic acid. The resultant benzamidohydroxamic acids VII can be converted into the aldehydes I according to the invention by reduction, using, for example, lithium aluminum hydride as reducing agent at from −60 to 0° C. in inert solvents such as tetrahydrofuran or ether.

Similar to the last process, it is also possible to prepare benzamidocarboxylic acids or acid derivatives IX such as esters or amides which may also be converted into the aldehydes I according to the invention by reduction. These processes are listed in R. C. Larock, Comprehensive Organic Transformations, VCH Publisher, (1989), page 619–26.

The benzamidoaldehydes I are inhibitors of cysteine proteases such as calpain I and II and cathepsin B and L and may thus serve to control disorders which are linked to an increased enzyme activity of the calpain enzymes and/or the cathepsin enzymes. The present benzamidoaldehydes I can therefore be used for the treatment of neurodegenerative disorders which occur after ischemia, trauma, subarachnoidal bleeding and/or stroke, and/or of neurodegenerative disorders such as multiple infarct dementia, Alzheimer's disease and/or Huntington's disease, and/or furthermore for the treatment of damage to the heart after cardial ischemia, damage to the kidneys after renal ischemia, damage to the skeletal muscles, muscular dystrophies, damage caused by the proliferation of the smooth muscle cells, coronal vasospasms, cerebral vasospasms, cataracts of the eyes and/or of restenosis of the blood vessels after angioplasty. Additionally, the benzamidoaldehydes I can be useful in the chemotherapy of tumors and their metastases, and/or in the treatment of disorders where increased interleukin-1 levels occur, such as inflammations and/or rheumatic disorders.

The inhibitory activity of the benzamidoaldehydes I was determined using enzyme tests which are customarily used in the literature, determining as a measure of activity the concentration of the inhibitor where 50% of the enzyme activity is inhibited (=$IC_{50}$). In this manner, the benzamidoaldehydes I were investigated for their inhibitory activity to calpain I, calpain II and cathepsin B.

Cathepsin B Test

The inhibition of cathepsin B was determined similar to a method of S. Hasnain et al., J.Biol.Chem. 268 (1993), 235–40. 2 μl of an inhibitor solution prepared from inhibitor and DMSO (final concentrations: 100 μm to 0.01 μm) were added to 88 μl of cathepsin B (cathepsin B from human liver) (Calbiochem), diluted to 5 units in 500 μM buffer). This experiment was preincubated for 60 minutes at room temperature (25° C.), and the reaction was then started by adding 10 μl of 10 mM Z-Arg-Arg-pNA (in a buffer containing 10% DMSO). The reaction was monitored for 30 minutes at 405 nm in the microtiter plate reader. The $IC_{50}$-values were then determined from the maximum slopes.

Calpain I and II Test

The inhibitory properties of calpain inhibitors were studied in a buffer containing 50 mM of Tris-HCl, pH 7.5; 0.1 M of NaCl; 1 mM of dithiotreithol; 0.11 mM of $CaCl_2$, using the fluorogenic calpain substrate Suc-Leu-Tyr-AMC (25 mM dissolved in DMSO, Bachem/Switzerland) (Sasaki et al. J. Biol. Chem. 1984, Vol. 259, 12489–12494). Human μ-calpain is isolated from erythrocytes similarly to the methods of Croall and DeMartino (BBA 1984, Vol. 788, 348–355) and Graybill et al. (Bioorg. & Med. Lett. 1995, Vol. 5, 387–392). After several chromatographic steps (DEAE-Sepharose, Phenyl-Sepharose, Superdex 200 and Blue-Sepharose), the enzyme is obtained in a purity of <[sic] 95%, according to SDS-PAGE, Western blot analysis and N-terminal sequencing. The fluorescence of the cleavage product 7-amino-4-methylcoumarin (AMC) is monitored in a Spex-Fluorolog fluorimeter at $\lambda_{ex}$=380 nm an $\lambda_{em}$=460 nm. Over a measured range of 60 min, the cleavage of the substrate is linear and the autocatalytic activity of calpain is low when the experiments are carried out at 12° C. (see Chatterjee et al. 1996, Bioorg. & Med. Chem. Lett., Vol 6, 1619–1622). Inhibitors and calpain substrate are added to the experiment as DMSO solutions, and the final concentration of DMSO should not exceed 2%.

In a typical experiment, 10 μl of substrate (250 μm final) and then 10 μl of μ-calpain (2 μg/ml final, i.e. 18 nM) are added to a 1 ml cuvette containing buffer. The calpain-mediated cleavage of the substrate is measured for 15 to 20 min. 10 μl of inhibitor (50 or 100 μM of DMSO solution) are subsequently added and the inhibition of cleavage is measured for a further 40 min. $K_i$ values are determined according to the conventional equation for reversible inhibition, i.e. $K:=1(v_0/v_i)-1$ [sic]; where I=inhibitor concentration, $v_0$=initial rate prior to addition of inhibitor; $v_i$=reaction rate at equilibrium.

For 2-phenyl-N-(3-phenylpropan-1-al-2-yl)benzamide (Example 30), a $K_i$ of <0.5 μM was determined. This derivative is therefore significantly more effective than the very closely related N-(1-3-phenylpropan-1-al-2-yl) benzamide (from M. R. Angelastro et al., J. Med. Chem. 1990, 33, 11–13).

Calpain-mediated breakdown of tyrosine kinase pp60src in platelets

After the activation of platelets, tyrosine kinase pp60src was cleaved by calpain. This was thoroughly investigated by Oda et al. in J. Biol. Chem., 1993, Vol 268, 12603–12608. It was shown that the cleavage of pp60src can be inhibited by calpeptin, an inhibitor of calpain. In accordance with this publication, the cellular efficacy of the novel substances was tested. Fresh human blood which had been treated with citrate was centrifuged at 200 g for 15 min. The platelet-enriched plasma was pooled and diluted 1:1 with platelet buffer (platelet buffer: 68 mM of NaCl, 2.7 mM of KCl, 0.5 mM of $MgCl_2 \times 6H_2O$, 0.24 mM of $NaH_2PO_4 \times H_2O$, 12 mM of $NaHCO_3$, 5.6 mM of glucose, 1 mM of EDTA, pH 7.4). After one centrifugation and wash step using platelet buffer, the platelets were adjusted to $10^7$ cells/ml. The isolation of the human platelets was carried out at room temperature.

In the experiment, isolated platelets ($2 \times 10^6$) were preincubated with different concentrations of inhibitors (dissolved in DMSO) at 37° C. for 5 min. The platelets were subsequently activated using 1 μM of ionophore A23187 and 5 mM of $CaCl_2$. After 5 min of incubation, the platelets were briefly centrifuged at 13000 rpm and the pellet was suspended in SDS sample buffer (SDS sample buffer: 20 mM of Tris-HCl, 5 mM of EDTA, 5 mM of EGTA, 1 mM of DTT, 0.5 mM of PMSF, 5 μg/ml of leupeptin, 10 μm of pepstatin, 10% of glycerol and 1% of SDS). The proteins were separated in a 12% gel and pp60src and its 52 kDa and 47 kDa cleavage products were identified by Western blotting. The polyclonal rabbit antibody anti-Cys-src ($pp60^{c-src}$) used was purchased from Biomol Feinchemikalien (Hamburg, FRG). This primary antibody was detected using an HRP-coupled second antibody from goat (Boehringer Mannheim, FRG). The Western blotting was carried out according to known methods.

The cleavage of pp60src was quantified densitometrically using non-activated (control 1: no cleavage) and ionophore- and calcium-treated platelets (control 2: corresponds to 100% cleavage) as controls. The $ED_{50}$ value corresponds to that concentration of inhibitor where the intensity of the color reaction of the 60 kDa band corresponds to the value intensity of control 1 plus control 2 divided by 2.

Glutamate-induced cell death in cortical neurons

The test was carried out in analogy to D. W. Choi, M.A. Maulucci-Gedde and A. R. Kriegstein, "Glutamate neurotoxicity in cortical cell culture", J.Neurosci. 7 (1987), 357–368. Cortex hemispheres were isolated from 15-day-old mouse embryos, and the individual cells were obtained enzymatically (trypsin). These cells (glia and cortical neurons) were sown in 24 well plates. After three days (laminin-coated plates) or seven days (ornithine-coated plates), the mitosis treatment was carried out using FDU (5-fluoro-2-deoxyuridine). 15 days after the cell preparation, cell death was induced by the addition of glutamate (15 minutes). After the glutamate has been removed, the calpain inhibitors are added. 24 hours later, the damage to the cells was evaluated by determining the lactate dehydrogenase (LDH) in the supernatant of the cell culture.

Calcium-mediated cell death in NT2 cells

In the human cell line NT2 (precursor cells, Stratagene GmbH), cell death can be induced by calcium in the presence of the ionophore A23187. $10^5$ cells/well were placed into microtiter plates 20 hours prior to the experiment. After this time, the cells were incubated with various concentrations of inhibitors in the presence of 2.5 μmol of ionophore and 5 μmol of calcium. After 5 hours, 0.05 ml of XTT (Cell Proliferation Kit II, Boehringer Mannnheim) were added to the experiment. Approximately 17 hours later, the optical density was determined using the Easy Reader EAR 400 (SLT) according to the specifications of the manufacturer. The optical density at which half of the cells have died is calculated from the two control experiments with cells without inhibitors which were incubated in the presence and absence of ionophore.

In a series of neurological disorders or mental disorders, an increased glutamate activity is encountered leading to overexcitation or toxic effects in the central nervous system (CNS).

Substances which inhibit the effects mediated by glutamate can therefore be employed in the treatment of these diseases. Glutamate antagonists, and these include in particular NMDA antagonists or their modulators and AMPA antagonists, are suitable for therapeutic use as drugs for neurodegenerative disorders (Huntington's chorea and Parkinson's disease), neurotoxic disorders after hypoxia, anoxia and ischemia as encountered after strokes, or else as antiepileptics, antidepressants and anxiolytics (cf. Arzneim. Forschung 1990, 40, 511–514; TIPS, 1990, 11, 334–338 and Drugs of the Future 1989, 14 (11), 1059–1071).

Intracerebral administration of excitatory amino acids (=EAA) induces such a massive overexcitation that within a short period of time spasms set in leading to the death of the animals. These symptoms can be inhibited by systemic—for example intraperitoneal—administration of centrally acting EAA antagonists. Since the excessive activation of EAA receptors of the central nervous system plays an important role in the pathogenesis of various neurological disorders, an established EAA antagonism in vivo can be seen as an indication for the therapeutic suitability of the substances against such CNS disorders. These include, inter alia, focal and global ischaemias, trauma, epilepsies and various neurodegenerative disorders such as Huntington's chorea, Parkinson's disease, etc.

It has already been shown that calpain inhibitors in cell cultures also have protective activity against cell death triggered by EAA (H. Cauer et al., Brain Research 1993, 607, 354–356; Yu Cheg and A. Y. Sun, Neurochem. Res. 1994, 19, 1557–1564). Surprisingly, the calpain inhibitors embraced by this application are active even against spasms triggered by EAA (for example NMDA or AMPA) and therefore indicate a therapeutic use in the abovementioned CNS disorders.

The drug preparations according to the invention comprise a therapeutically active amount of the compounds I in addition to the conventional drug auxiliaries.

For local external applications, for example in powders, ointments or sprays, the active compounds may be present in customary concentrations. The active compounds are generally present in an amount of from 0.001 to 1% by weight, preferably from 0.01 to 0.1% by weight.

When applied internally, the preparations are administered in single doses containing from 0.1 to 100 mg per kg of body weight. The preparations may be administered daily in one or more doses depending on the type and severity of the diseases.

Depending on the desired method of application, the drug preparations according to the invention comprise the customary carriers and diluents, in addition to the active compound. Suitable for local external application are pharmaceutical auxiliaries, such as ethanol, isopropanol, ethoxylated castor oil, ethoxylated hydrogenated castor oil, polyacrylic acid, polyethylene glycol, polyethylene glycol stearate, ethoxylated fatty alcohols, paraffin oil, paraffin jelly and lanolin. Suitable for internal administration are for example lactose, propylene glycol, ethanol, starch, talc and polyvinylpyrrolidone.

The preparations may further comprise antioxidants, such as tocopherol and butylated hydroxyanisol and butylated hydroxytoluene, additives which improve the flavor, stabilizers, emulsifiers and lubricants.

The compounds which are present in the preparation in addition to the active compound and the compounds used in the production of the pharmaceutical preparations are nontoxic and compatible with the respective active compound. The drug preparations are produced in a conventional manner, for example by mixing the active compound with other conventional carriers and diluents.

The drug preparations may be administered in various ways, for example orally, parenterally, such as intravenously by infusion, subcutaneously, intraperitoneally and topically. Preparation forms such as tablets, emulsions, solutions for infusions and injections, pastes, ointments, gels, creams, lotions, powders and sprays are possible.

EXAMPLES

Example 1

N-(Butan-1-al-2-yl)-2-((E-2-phenylethen-1-yl)amido)benzamide

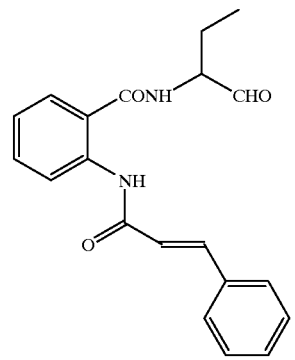

a) 2-Amino-N-(butan-1-ol-2-yl)benzamide 10.0 g (61 mmol) of isatoic anhydride and 11 g (123.6 mmol) of 2-amino-1-butanol in 200 ml of tetrahydrofuran were heated under reflux for 8 hours. The tetrahydrofuran was then removed under reduced pressure and the resulting residue was distributed between 2M aqueous sodium hydroxide solution and ethyl acetate. The ethyl acetate phase was dried and concentrated under reduced pressure. 10.5 g (82%) of the product were obtained.

b) N-(Butan-1-ol-2-yl)-2-((E-2-phenylethen-1-yl)amido)benzamide 1 g (5 mmol) of the above intermediate 1a and 0.6 g (6 mmol) of triethylamine were dissolved in 50 ml of tetrahydrofuran. At 0° C., 0.95 g (5.7 mmol) of cinnamoyl chloride dissolved in a little tetrahydrofuran was added dropwise in such a way that the temperature remained below 5° C. The mixture was stirred for 1 h. The reaction was then concentrated under reduced pressure and the residue was distributed between 2M aqueous sodium hydroxide solution and ethyl acetate. The organic phase was dried and concentrated under reduced pressure. This crude product was boiled in ether and then filtered with suction. 1.1 g (56%) of the product were obtained.

c) N-(Butan-1-al-2-yl)-2-((E-2-phenylethen-1-yl)amido)benzamide 1.1 g (14 mmol) of dimethyl sulfoxide dissolved in 5 ml of methylene chloride were slowly added dropwise to 0.9 g (7 mmol) of oxalyl chloride in 25 ml of anhydrous methylene chloride at from −60 to −500° C. The mixture was stirred for 15 minutes. 2 g (6 mmol) of the intermediate 1b dissolved in 10 ml of methylene chloride were then added dropwise in such a way that the temperature remained below −50° C. The mixture was then stirred for a further 30 min. 1.5 g (15 mmol) of triethylamine were then added and the mixture was warmed to room temperature. The reaction mixture was washed with water and the organic phase was dried and concentrated under reduced pressure. The residue was treated with ether and filtered with suction. 0.4 g (20%) of the product was obtained.

MS: m/e=336 (M⁺).

Example 2

N-(Butan-1-al-2-yl)-2-((2-naphthyl)amido)benzamide

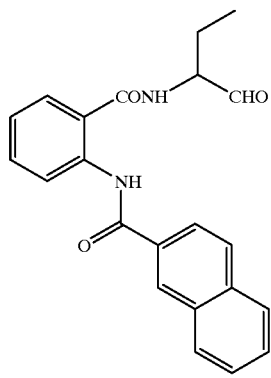

a) N-(Butan-1-ol-2-yl)-2-((2-naphthyl)amido)benzamide 1 g (4.8 mmol) of the intermediate 1a and 0.95 g (5 mmol) of 2-naphthoyl chloride were reacted by the method of procedure 1b. 1.05 g (62%) of the product were obtained.

b) N-(Butan-1-al-2-yl)-2-((2-naphthyl)amido)benzamide 0.9 g (2.5 mmol) of the intermediate 2a were oxidized by the method of procedure 1c using dimethyl sulfoxide/oxalyl chloride. After chromatographic purification (eluent: toluene/acetone=17/3), 78 mg (9%) of the product were obtained.

$^1$H-NMR(D$_6$-DMSO): δ=1.0 (3H); 1.6–2.0 (2H); 4.3 (1H); 7.2–8.8(11H); 9.0 (1H); 9.7(1H) and 12.1(1H)ppm.

Example 3

N-(Butan-1-al-2-yl)-3-((2-naphthyl)amido)benzamide

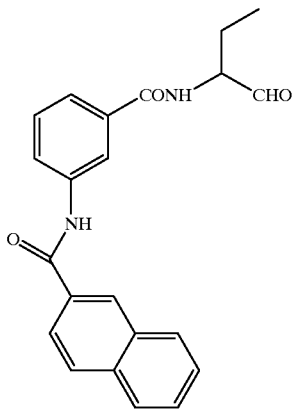

a) N-(3-Ethoxycarbonylphenyl)-2-naphthoylamide 6.6 ml of triethylamine and, at 0–5° C., 9 g (47.5 mmol) of 2-naphthoyl chloride dissolved in 50 ml of tetrahydrofuran were added successively to 7.5 g (45.5 mmol) of ethyl 3-aminobenzoate dissolved in 150 ml of tetrahydrofuran. The mixture was stirred for about 1 h. The mixture was then filtered and the residue was concentrated under reduced pressure. The resulting solid was treated with ether and filtered with suction once more. 9.3 g (64%) of the product were obtained.

b) 3-(2-Naphthylamido)benzoic acid 9.0 g (28 mmol) of the product 3a were dissolved in 100 ml of tetrahydrofuran and treated with 2.7 g (113 mmol) of lithium hydroxide dissolved in 50 ml of water. The mixture was stirred at room temperature until the reaction had ended (about 6 h). The tetrahydrofuran was then removed under reduced pressure and the resulting aqueous phase was acidified using 2M hydrochloric acid. The precipitate was filtered off with suction. 7.8 g (95%) of the product were obtained.

c) N-(Butan-1-ol-2-yl)-3-((2-naphthyl)amido)benzamide

At 0° C., 0.8 g (7.7 mmol) of ethyl chloroformate dissolved in a little tetrahydrofuran was added dropwise to 2 g (6.9 mmol) of the intermediate 3b and 0.8 g (7.9 mmol) of triethylamine dissolved in 50 ml of anhydrous tetrahydrofuran. At -20 to -10° C., 0.6 g (6.7 mmol) of 2-aminobutanol were then added dropwise. The mixture was stirred at room temperature for 16 h. The tetrahydrofuran was then removed under reduced pressure and the residue was distributed between water and ethyl acetate. The organic phase was dried and concentrated under reduced pressure. The product was boiled with ether and filtered with suction. 1.5 g (58%) of the product were obtained.

d) N-(Butan-1-al-2-yl)-3-(2-naphthylamido)benzamide 1.3 g (3.5 mmol) of the intermediate 3c were oxidized by the method of the procedure 1c using dimethyl sulfoxide/oxalyl chloride. After a chromatographic purification (eluent: toluene/acetone=1/1), 0.24 g (18%) of the product was obtained.

$^1$H-NMR(D$_6$-DMSO): δ=1.0(3H); 1.6–2.0 (2H); 4.2(1H), 7.3–8.8 (10H); 8.9(1H), 9.4(1H) and 10.5(1H)ppm.

Example 4

(S)-N-(3-Phenylpropan-1-al-2-yl)-2-(3-pyridyl)amidobenzamide

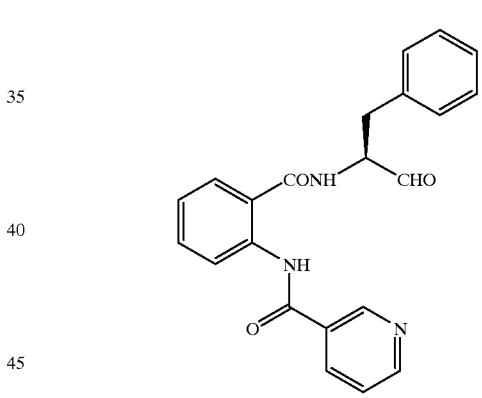

a) (S)-2-Amino-N-(3-phenylpropan-1-ol-2yl)benzamide

The product was prepared by the method of procedure 1a from 5 g (S)-(-)-2-amino-3-phenyl-1-propanol and isatoic anhydride. 3.6 g of the product were obtained.

b) (S)-N-(3-Phenylpropan-1-ol-2-yl)-2-(3-pyridyl)amidobenzamide 1.0 g (3.7 mmol) of the intermediate 4a was dissolved in 25 ml of pyridine and, at 0° C., mixed a little at a time with 0.7 g (3.9 mmol) of nicotinoyl chloride hydrochloride. The reaction mixture was stirred for a number of hours (DC control). The mixture was then concentrated under reduced pressure. The resulting crude product (about 2 g) was used as such for further reactions.

c) (S)-N-(3-Phenylpropan-1-al-2-yl)-2-(3-pyridyl)amidobenzamide 2 g of the intermediate 4b were oxidized by the method of procedure 1c using dimethyl sulfoxide/oxalyl chloride. After chromatographic purification (eluent: toluene/acetone=1/1), 0.17 g of the product was obtained.

MS: m/e=373 (M$^+$).

Example 5

(S)-N-(3-Phenylpropan-1-al-2-yl)-2-(2-naphthyl)amidobenzamide

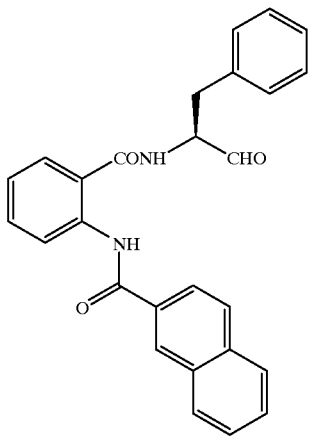

a) (S)-N-(3-Phenylpropan-1-ol-2-yl)-2-(2-naphthyl)amidobenzamide 1.5 g (5.6 mmol) of the intermediate 4a were reacted with 1.2 g (6.3 mmol) of naphthoyl chloride by the method of the procedure 4b. 1.4 g (58%) of the product were obtained.

b) (S)-N-(3-Phenylpropan-1-al-2-yl)-2-(2-naphthylamido)benzamide 1.2 g (4.7 mmol) of the intermediate 5a were oxidized by the method of procedure 1c using oxalyl chloride/dimethyl sulfoxide. 0.5 g (42%) of the product was obtained.

MS: m/e=422(M$^+$).

Example 6

(S)-N-(3-Phenylpropan-1-al-2-yl)-3-(2-naphthyl)amidobenzamide

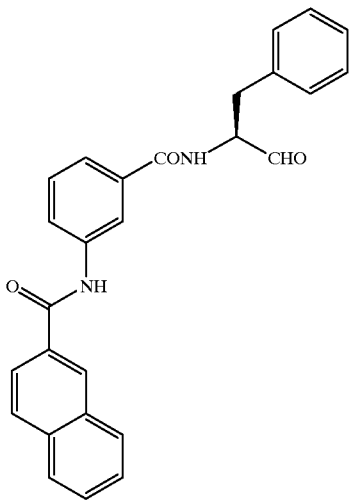

a) (S)-N-(3-Phenylpropan-1-ol-2-yl)-3-(2-naphthylamido)benzamide 2 g (6.8 mmol) of the intermediate 3b were reacted with (S)-2-amino-3-pheyl-1-propanol [sic] by the method of procedure 3c. 1 g (34%) of the product was obtained.

b) (S)-N-(3-Phenylpropan-1-al-2-yl)-3-(2-naphthyl)amidobenzamide 0.9 g (2.1 mmol) of the intermediate 6a was oxidized with dimethyl sulfoxide/oxalyl chloride by the method of procedure 1c. After chromatographic purification (eluent: toluene/acetone=3/1), 0.2 g (22%) of the product was obtained.

MS: m/e=422(M$^+$).

Example 7

(S)-2-(2-Phenyl-1-ethyl)amido-N-(3-phenylpropan-1-al-2-yl)benzamide

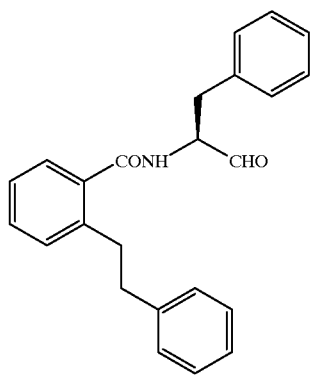

a) (S)-2-(2-Phenyl-1-ethyl)amido-N-(3-phenylpropan-1-al-2-yl)benzamide 0.3 g (2.2 mmol) of N-hydroxybenzotriazole (HOBT) and, a little at a time, 1.3 g (6.6 mmol) of N-(3-dimethylaminopropyl)-N-ethylcarbodiimide (EDC) were added successively to 1.5 [lacuna] (6.6 mmol) of 2-(2-phenyl-1-ethyl)benzoic acid, 1.0 g (6.6 mmol) of (S)-2-amino-3-phenylpropan-1-ol and 1.4 ml (9.9 mmol) of triethylamine in 50 ml of methylene chloride. The mixture was stirred at room temperature for 16 h. The reaction mixture was then diluted with a large volume of ethyl acetate and washed successively twice with 2M hydrochloric acid, twice with 2M aqueous sodium hydroxide solution and three times with water. The organic phase was dried and concentrated under reduced pressure. The residue was precipitated from methylene chloride/petroleum ether. 1.85 g (79%) of the product were obtained.

b) (S)-2-(2-Phenyl-1-ethyl)amido-N-(3-phenylpropan-1-al-2-yl)benzamide 1.6 g (4.5 mmol) of the intermediate 7a were oxidized with dimethyl sulfoxide/oxalyl chloride by the method of procedure 1c. 0.7 g (46%) of the product was obtained.

$^1$H-NMR (CDCl$_3$): δ=2.8–3.4(6H); 4.9(1H); 6.1(1H); 7.0–7.6(14H) and 9.8(1H)ppm

Example 8

(S)-3-Benzoyl-N-(3-phenylpropan-1-al-2-yl)benzamide

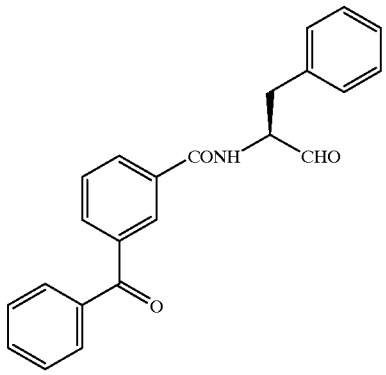

a) (S)-3-Benzoyl-N-(3-phenylpropan-1-ol-2-yl)benzamide 2 g (8.8 mmol) of 3-benzoylbenzoic acid were reacted with (S)-2-amino-3-phenyl-1-propanol by the method of procedure 3c. 2.5 g (79%) of the product were obtained.

b) (S)-3-Benzoyl-N-(3-phenylpropan-1-al-2-yl)benzamide 2 g (5.6 mmol) of the intermediate 8a were oxidized by the method of procedure 1c. After chromatographic purification (eluent: methylene chloride/methanol=10:1), 1.2 g (61%) of the product were obtained.

MS: m/e=357(M+).

Example 9

(S)-2-Benzoyl-N-(3-phenylpropan-1-al-2-yl)benzamide

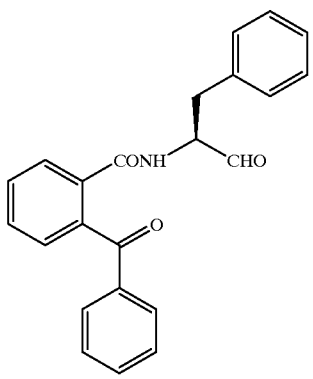

a) (S)-2-Benzoyl-N-(3-phenylpropan-1-ol-2-yl)benzamide

2-Benzoylbenzoic acid was reacted with (S)-2-amino-3-phenyl-1-propanol by the method of procedure 3c. 2.6 g (86%) of the product were obtained.

b) (S)-2-Benzoyl-N-(3-phenylpropan-1-al-2-yl)benzamide 2.4 g (6.7 mmol) of the intermediate 9a were oxidized with dimethyl sulfoxide/oxalyl chloride by the method of procedure 1c. After chromatographic purification (eluent= toluene/ethyl acetate=20/1), 0.5 g (21%) [lacuna] was obtained.

MS: m/e=357 (M+).

Example 10

(S)-3-(1-Naphthyl)amido-N-(3-phenylpropan-1-al-2-yl)benzamide

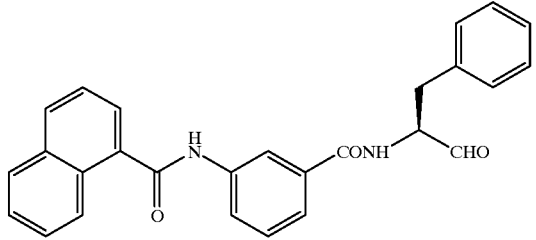

a) 3-(1-Naphthylamido)benzoic acid

At 0° C., 7.3 g (38 mmol) of 1-naphthoyl chloride dissolved in 25 ml of tetrahydrofuran were added dropwise to 5 g (36.5 mmol) of 3-aminobenzoic acid and 10 ml (73 mmol) of triethylamine in 100 ml of anhydrous tetrahydrofuran. The mixture was stirred at 0° C. for 1 h. The mixture was then concentrated under reduced pressure and the residue was distributed between ethyl acetate and 2M hydrochloric acid whereupon the product crystallized out. 7.8 g (74%) of the product were obtained.

b) (S)-3-(1-Naphthyl)amido-N-(3-phenylpropan-1-ol-2-yl)benzamide 1 g (3.4 mmol) of the intermediate 10a was reacted with (S)-2-amino-3-phenyl-1-propanol by the method of procedure 7a, affording 1.1 g (76%) of the product.

c) (S)-3-(1-Naphthyl)amido-N-(3-phenylpropan-1-al-2-yl)benzamide 1.0 g (2.3 mmol) of the intermediate 10b was oxidized with dimethyl sulfoxide/oxalyl chloride by the method of procedure 1c. 0.35 g (35%) of the product was obtained.

$^1$H-NMR(CDCl$_3$): δ=3.1(2H); 4.6(1H); 7.0–8.4(18H) and 9.6(1H)ppm.

Example 11

(S)-4-(2-Naphthyl)amido-N-(3-phenylpropan-1-al-2-yl)benzamide

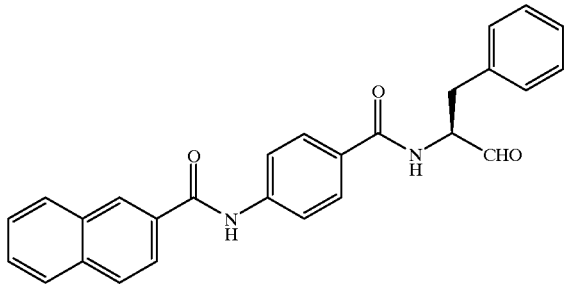

a) 4-(2-Naphthyl)amidobenzoic acid 5 g (36.5 mmol) of 4-aminobenzoic acid were reacted with 2-naphthoyl chloride by the method of procedure 10a, affording 6.6 g (62%) of the product.

b) (S)-4-(2-Naphthyl)amido-N-(3-phenylpropan-1-al-2-yl)benzamide 1 g (3.4 mmol) of the intermediate 11a was reacted with (S)-2-amino-3-phenyl-1-propanol by the method of procedure 7a. 0.9 g (62%) of the product was obtained.

c) (S)-4-(2-Naphthyl)amido-N-(3-phenylpropan-1-al-2-yl)benzamide 0.8 g (1.9 mmol) of the intermediate 11b was oxidized with dimethyl sulfoxide/oxalyl chloride by a method of procedure 1c. After chromatographic purification (eluent: methylene chloride/methanol=15/1), 0.4 g (53%) of the product was obtained.

$^1$H-NMR(D$_6$-DMSO): [lacuna]=2.9(1H); 3.3(1H); 4.5 (1H); 7.0–8.3 (14H); 8.6(1H); 8.8(1H); 9.6(1H) and 10.6 (1H)ppm.

Example 12

(S)-2-(2-Naphthyl)sulfonamido-N-(3-phenylpropan-1-al-2-yl)benzamide

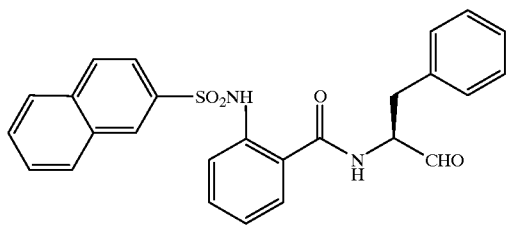

a) (S)-2-(2-Naphthyl)sulfonamido-N-(3-phenylpropan-1-ol-2-yl)benzamide 1.5 g (5.6 mmol) of (S)-2-amino-N-(3-phenylpropan-1-ol-2-yl)benzamide (intermediate 4a) were reacted with 2-naphthylsulfonyl chloride by the method of procedure 4b. 0.67 g of the product was obtained.

b) (S)-2-(2-Naphthyl)sulfonamido-N-(3-phenylpropan-1-al-2-yl)benzamide 0.6 g (1.3 mmol) of the intermediate 12a was oxidized with dimethyl sulfoxide/oxalyl chloride by the method of procedure 1c. After chromatographic purification (eluent: toluene/acetone=1/2), 0.4 g of the product was obtained.

MS: m/e=458(M$^+$).

Example 13

(S)-2-Benzyl-N-(3-phenylpropan-1-al-2-yl)benzamide

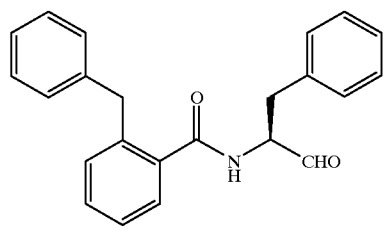

a) (S)-2-Benzyl-N-(3-phenylpropan-1-ol-2-yl)benzamide

At 0° C., 2.1 g (9.2 mmol) of 2-benzylbenzoyl chloride dissolved in a little methylene chloride were added dropwise to 1.3 g (8.6 mmol) of (S)-2-amino-3-phenylpropan-1-ol in 35 ml of methylene chloride and 20 ml of 2M aqueous sodium hydroxide solution. The mixture was stirred for about 30 min. The organic phase was separated off, dried and concentrated under reduced pressure. 2.7 g (91%) of the product were obtained.

b) (S)-2-Benzyl-N-(3-phenylpropan-1-al-2-yl)benzamide 2 g (5.8 mmol) of the intermediate 13a were oxidized with dimethyl sulfoxide/oxalyl chloride by the method of procedure 1c. 1.5 g (75%) of the product was obtained.

$^1$H-NMR(D$_6$-DMSO): δ=2.8(1H); 3.3(1H); 4.0(2H); 4.5 (1H); 7.0–7.5(1H); 8.8(1H) and 9.5(1H)ppm.

Example 14

(S)-6-Methyl-2-(2-naphthyl)amido-N-(3-phenylpropan-1-al-2-yl)benzamide

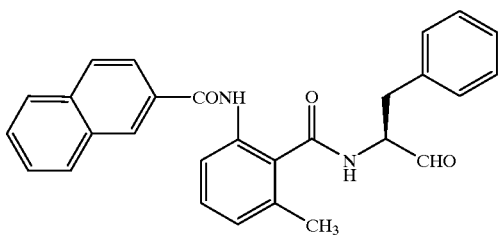

a) (S)-2-Aminomethyl-N-(3-phenylpropan-1-al-2-yl)benzamide 5 g (28.2 mmol) of 5-methylisatoic anhydride and 4.3 g (28.5 mmol) of (S)-2-amino-3-phenyl-1-propanol in 150 ml of tetrahydrofuran were heated at reflux for about 8 h. The mixture was then concentrated under reduced pressure and the residue was distributed between ethyl acetate and 2M aqueous sodium hydroxide solution. The organic phase was dried and once again concentrated under reduced pressure. This residue was then treated with ether, affording 3.2 g (39%) of the product.

b) (S)-6-Methyl-2-(2-naphthyl)amido-N-(3-phenylpropan-1-ol-2-yl)benzamide 2 g (7 mmol) of the intermediate 14a were reacted with 2-naphthoyl chloride by the method of procedure 10a. 2.7 g (77%) of the product were obtained.

(S)-6-Methyl-2-(2-naphthyl)amido-N-(3-phenylpropan-1-al-2-yl)benzamide 2 g (4.6 mmol) of the intermediate 14b were oxidized with dimethyl sulfoxide/trifluoroacetic anhydride by the method of procedure 1c. After chromatographic purification (eluent: tetrahydrofuran/toluene/ethyl acetate=5/10/5), 1 g (50%) of the product was obtained.

MS: m/e=436 (M$^+$).

Example 15

(S)-2-Phenyloxymethyl-N-(3-phenylpropan-1-al-2-yl)benzamide

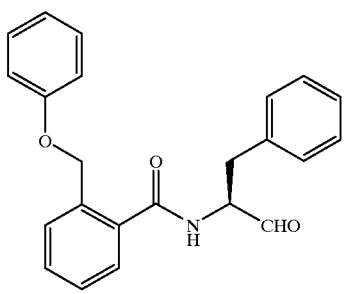

a) (S)-2-Phenyloxymethyl-N-(3-phenylpropan-1-ol-2-yl)benzamide 2 g (8.8 mmol) of 2-phenoxymethylbenzoic acid were reacted with (S)-2-amino-3-phenyl-1-propanol by the method of procedure 7a. 2.7 g (84%) of the product were obtained.

b) (S)-2-Phenyloxymethyl-N-(3-phenylpropan-1-al-2-yl)benzamide 2 g (5.5 mmol) of the intermediate 15a were oxidized with dimethyl sulfoxide/trifluoroacetic anhydride by the method of procedure 3c. After chromatographic purification (eluent: toluene/ethyl acetate=10/1), 1.6 g (79%) of the product were obtained.

MS: m/e=359(M+).

Example 16

(S)-4-Benzoyl-N-(3-phenylpropan-1-al-2-yl)benzamide

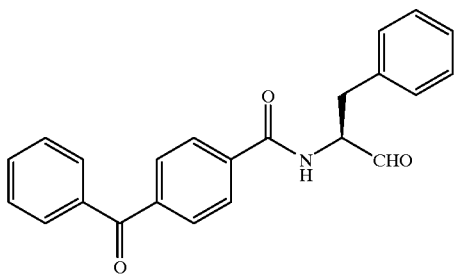

a) (S)-4-Benzoyl-N-(3-phenylpropan-1-ol-2-yl)benzamide 3 g (13 mmol) of benzophenone-4-carboxylic acid were reacted with (S)-2-amino-3-phenyl-1-propanol by the method of procedure 3c. 3.2 g (67%) of the product were obtained.

b) (S)-4-Benzoyl-N-(3-phenylpropan-1-al-2-yl)benzamide 2.4 g (6.7 mmol) of the intermediate 16a were oxidized with dimethyl sulfoxide/trifluroacetic [sic] anhydride by the method of procedure 3c. After chromatographic purification (eluent: toluene/tetrahydrofuran=10/1), 0.3 g (13%) of the product was obtained.

MS: m/e=357(M+).

Example 17

(S)-2-(E-2-Phenyl-1-ethenyl)-N-(3-phenylpropan-1-al-2-yl)benzamide

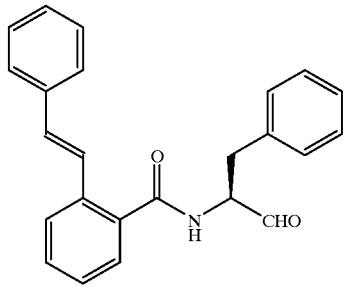

a) Ethyl 2-(E-2-phenyl-1-ethenyl)benzoate 8.9 g (38.9 mmol) of ethyl 2-bromobenzoate, 5.1 g (49.4 mmol) of styrene, 0.18 g (0.8 mmol) of palladium diacetate, 0.48 g (1.6 mmol) of tri-o-tolylphosphine and 5 g (49.1 mmol) of triethylamine were reacted in 90 ml of anhydrous acetonitrile at 100° C. for 23 h. The mixture was then filtered and the filtrate was diluted with ethyl acetate, washed with water, dried and concentrated under reduced pressure. 10.2 g (100%) of the product were obtained.

b) 2-(E-2-Phenyl-1-ethenyl)benzoic acid 10 g (39.5 mmol) of the intermediate 17a, together with 3.2 g (79 mmol) of sodium hydroxide in 100 ml of water, were heated under reflux for 10 h. The mixture was then diluted with water and washed with ether. The aqueous phase was acidified with 1M hydrochloric acid whereupon the product precipitated. 6.2 g (70%) of the product were obtained.

c) (S)-2-(E-2-Phenyl-1-ethenyl)-N-(3-phenylpropan-1-ol-2-yl)benzamide 1.0 g (4.5 mmol) of the intermediate 17b and 0.67 g (4.5 mmol) of (S)-2-amino-3-phenyl-1-propanol were reacted by the method of procedure 7a. 1.5 g (94%) of the product were obtained.

d) (S)-2-(E-2-Phenyl-1-ethenyl)-N-(3-phenylpropan-1-al-2-yl)benzamide 1.5 g (4.2 mmol) of the intermediate 17c were oxidized with dimethyl sulfoxide/trifluoroacetic anhydride by the method of procedure 1c. After chromatographic purification (eluent: methylene chloride/methanol=20/1), 0.85 g (58%) of the product were obtained.

MS: m/e=355 (M+).

Example 18

(S)-2-Phenylethynyl-N-(3-phenylpropan-1-al-2-yl)benzamide

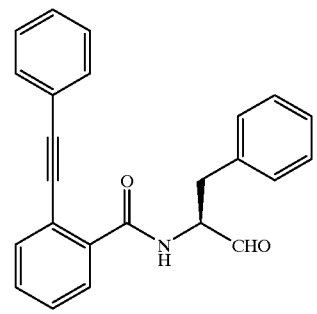

a) Ethyl 2-phenylethynylbenzoate 11.5 g (50.2 mmol) of ethyl 2-bromobenzoate, 6.15 g (60.2 mmol) of phenylacetylene, 0.16 g of bis(triphenylphosphino)palladium(II) dichloride and 0.08 g of copper(I) iodide in 10 ml of anhydrous triethylamine were heated under reflux for 6 hours. The reaction mixture was then diluted with ether, washed with water, dried and concentrated under reduced pressure. The residue was purified chromatographically (eluent: n-heptane/ethyl acetate=10/1), affording 11.3 [lacuna] (91%) of the product.

2-Phenylethynylbenzoic acid 11 g (44 mmol) of the intermediate 18a in 100 ml of tetrahydrofuran were admixed with 4.9 g (88 mmol) of potassium hydroxide dissolved in 200 ml of water, and the mixture was heated under reflux for 8 h. The tetrahydrofuran was then removed under reduced pressure and the aqueous phase that remained was washed with ether. The aqueous phase was acidified with dilute hydrochloric acid and extracted with ethyl acetate. After drying and concentrating, 9.5 g (98%) of the product were obtained.

c) (S)-2-Phenylethynyl-N-(3-phenylpropan-1-ol-2-yl)benzamide 2 g ([lacuna] mmol) of the intermediate 18b were reacted with (S)-2-amino-3-phenyl-1-propanol by the method of procedure 7a, affording 1.2 g (38%) of the product after chromatographic purification (eluent: toluene/acetone=10/1).

d) (S)-2-Phenylethynyl-N-(3-phenylpropan-1-al-2-yl)benzamide 1.0 g (2.8 mmol) of the intermediate 18c was oxidized with dimethyl sulfoxide/trifluoroacetic anhydride by the method of procedure 1c. After chromotographic purification (eluent: methylene chloride/ethyl acetate=10/1), 0.14 g (14%) of the product was obtained.

MS: m/e=353(M+).

Example 19

(S)-2-(2-Naphthylmethyloxy)-N-(3-phenylpropan-1-al-2-yl)benzamide

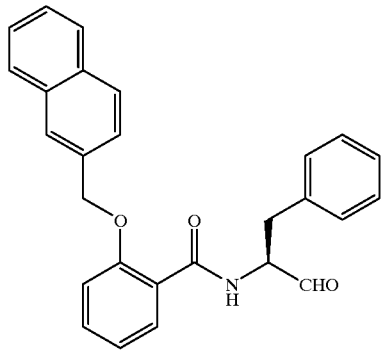

a) Methyl 2-(2-naphthylmethyloxy)benzoate 3.9 g (35 mmol) of potassium tert-butoxide were added a little at a time to 5 g (33 mmol) of methyl salicylate in 200 ml of dimethylformamide). After about 15 min, 7.3 g (33 mmol) of 2-(bromomethyl)naphthalene were added and the reaction mixture was heated to 100° C. for about 3 h. The reaction mixture was then poured into ice-water and the product was extracted with ethyl acetate. The organic phase was dried and concentrated under reduced pressure. 9.15 g (95%) of the product were obtained.

b) 2-(Naphthylmethyloxy)benzoic acid 8 g (3.4 mmol) of the intermediate 19a were hydrolyzed by the method of procedure 3b. 7 g (64%) of the product were obtained.

c) (S)-2-(2-Naphthylmethyloxy)-N-(3-phenylpropan-1-ol-2-yl)benzamide 2.45 g (8.8 mmol) of the intermediate 19b were reacted with (S)-2-amino-3-phenyl-1-propanol by the method of procedure 7a, affording 1.1 g (28%) of the product after chromatographic purification (eluent: toluene/tetrahydrofuran/triethylamine=20/10/1).

d) (S)-2-(2-Naphthylmethyloxy)-N-(3-phenylpropan-1-al-2-yl)benzamide 1.5 g (3.6 mmol) of the intermediate 19c were oxidized with dimethyl sulfoxide/trifluoroacetic anhydride by the method of procedure 1c. 1.3 g (87%) of the product were obtained.

$^1$H-NMR(D$_6$-DMSO): δ=2.9(1H); 3.2(1H); 4.6(1H); 5.3 (2H); 6.9–8.1(16H); 8.6(1H) and 9.6(1H)ppm.

Example 20

(S)-4-(2-Naphthylmethyloxy)-N-(3-phenylpropan-1-al-2-yl)benzamide

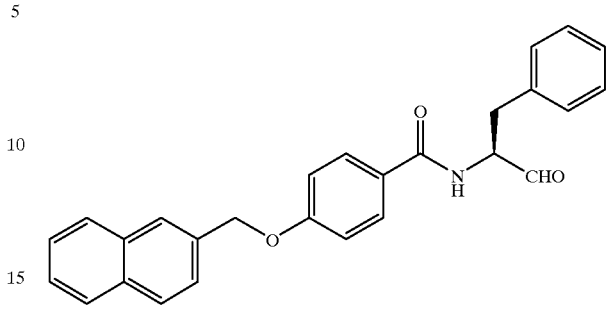

a) Methyl 4-(2-naphthylmethyloxy)benzoate 3.9 g (35 mmol) of potassium tert-butoxide were added a little at a time to 5 g (33 mmol) of methyl hydroxybenzoate in 200 ml of dimethylformamide. After about 15 min, a further 7.3 g (33 mmol) of 2-(bromomethyl)naphthalene were added and the reaction mixture was heated to 100° C. for about 3 h. The reaction mixture was then poured into ice-water and the product was extracted with ethyl acetate. The organic phase was dried and concentrated under reduced pressure. 8.4 g (88%) of the product were obtained.

b) 4-(2-Naphthylmethyloxy)benzoic acid 8 g (3.4 mmol) of the intermediate 20a were hydrolyzed by the method of procedure 3b. 2.3 g (30%) of the product were obtained.

c) (S)-4-(2-Naphthylmethyloxy)-N-(3-phenylpropan-1-ol-2-yl)benzamide 2.3 g (8.3 mmol) of the intermediate 20b were reacted with (S)-2-amino-3-phenyl-1-propanol by the method of procedure 7a, affording 2.95 g (87%) of the product.

d) (S)-2-(2-Naphthylmethyloxy)-N-(3-phenylpropan-1-al-2-yl)benzamide 1.5 g (3.6 mmol) of the intermediate 20c were oxidized with dimethyl sulfoxide/trifluoroacetic anhydride by the method of procedure 1c. 0.96 g (64%) of the product was obtained.

$^1$H-NMR(D$_6$-DMSO): δ=2.9(1H); 3.2(1H); 4.3(1H); 5.3 (2H); 7.0–8.0(16H); 8.6(1H) and 9.5(1H)ppm.

Example 21

(S)-4-(2-Naphthylamido)methyl-N-(3-phenylpropan-1-al-2-yl)benzamide

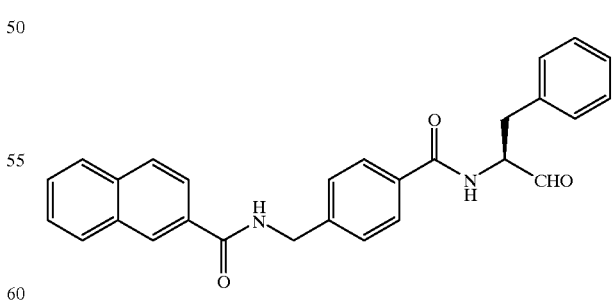

a) 4-(2-Naphthylamido)methylbenzoic acid 2.5 g (15.5 mmol) of 4-aminomethylbenzoic acid and 2-naphthoyl chloride were reacted by the method of procedure 4b, affording 2.1 g (42%) of the product.

b) (S)-4-(2-Naphthylamido)methyl-N-(3-phenylpropan-1-ol-2-yl)benzamide 1.4 g (4.6 mmol) of the intermediate 21a were reacted with (S)-2-amino-3-phenyl-1-propanol by the method of procedure 3c, affording 1.1 g (55%) of the product.

c) (S)-4-(2-Naphthylamido)methyl-N-(3-phenylpropan-1-al-2-yl)benzamide 0.8 g (1.8 mmol) of the intermediate 21b and 1.0 ml (7.3 mmol) of triethylamine were dissolved in 10 ml of anhydrous dimethyl sulfoxide and treated with 1.16 g (7.3 mmol) of sulfur trioxide-pyridine complex dissolved in 10 ml of dimethyl sulfoxide. The mixture was stirred at room temperature for 16 h. The mixture was then poured into water and the precipitate was filtered off with suction. 0.65 g (82%) of the product was obtained.

$^{1}$H-NMR(D$_{6}$-DMSO): δ=2.9(1H); 3.3(1H); 4.5(1H), 4.6 (2H); 7.1–8.1 (15H); 8.5(1H); 8.8(1H); 9.2(1H) and 9.6 (1H)ppm.

Example 22

(S)-3-(2-Naphthyl)sulfonamido-N-(3-phenylpropan-1-al-2-yl)benzamide

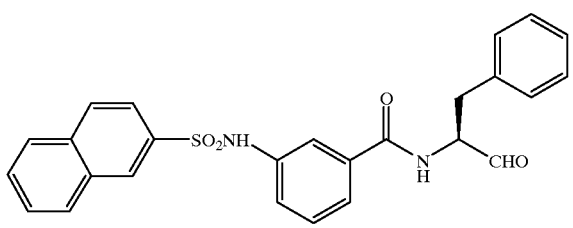

a) 3-(2-Naphthylsulfonamido)benzoic acid 5 g (35.5 mmol) of 3-aminobenzoic acid and 8.3 g (36.5 mmol) of 2-naphthylsulfonyl chloride were reacted by the method of procedure 4b, affording 10.5 g (89%) of the product.

b) (S)-3-(2-Naphthyl)sulfonamido-N-(3-phenylpropan-1-ol-2-yl)benzamide 1 g (3.1 mmol) of the intermediate 22a was reacted with (S)-2-amino-3-phenyl-1-propanol by the method of procedure 7a, affording 1.2 g (86%) of the product.

c) (S)-3-(2-Naphthyl)sulfonamido-N-(3-phenylpropan-1-al-2-yl)benzamide 1.0 g (2.2 mmol) of the intermediate 22b was oxidized with dimeth [sic] sulfoxide/oxalyl chloride by the method of procedure 1c.

MS: m/e=458(M$^{+}$).

Example 23

(S)-2-(2-Naphthyl)amido-4-nitro-N-(3-phenylpropan-1-al-2-yl)benzamide

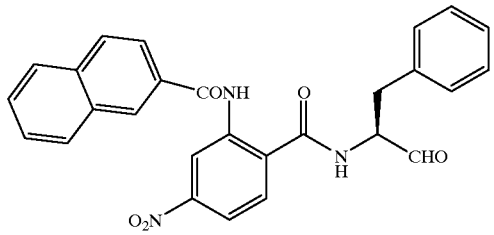

a) 2-(2-Naphthylamido)-4-nitro-benzoic acid 20 g (0.11 mmol) of 2-amino-4-nitrobenzoic acid were reacted with 2-naphthylbenzoyl chloride by the method of procedure 4b, affording 22.3 g (61%) of the product.

b) (S)-2-(2-Naphthyl)amido-4-nitro-N-(3-phenylpropan-1-ol-2-yl)benzamide 2 g (59.5 mmol) of the intermediate 23a were reacted with (S)-2-amino-3-phenyl-1-propanol by the method of procedure 3c, affording 2.5 g (90%) of the product.

c) (S)-2-(2-Naphthyl)amido-4-nitro-N-(3-phenylpropan-1-al-2-yl)benzamide 1.1 g (2.3 mmol) of the intermediate 23b were oxidized by the method of procedure 21c, affording 1.0 g (92%) of the product.

MS: m/e=467 (M$^{+}$).

Example 24

(S)-4-(8-Quinolinylsulfonamido)-N-(3-phenylpropan-1-al-2-yl)benzamide

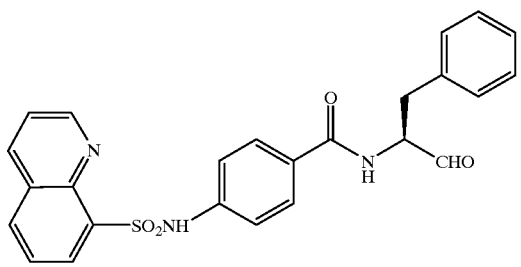

a) Ethyl 4-(8-quinolinesulfonylamido)benzoate 2 g (12 mmol) of ethyl 4-aminobenzoate were reacted with 8-quinolinesulfonyl chloride by the method of procedure 10a, affording 3.5 g (82%) of the product.

b) 4-(8-Quinolinesulfonylamido)benzoic acid 3.3 g (9.3 mmol) of the intermediate 24a and 1.6 g (27.8 mmol) of potassium hydroxide in 100 ml of water were heated to 95° C. for 45 min. The mixture was then neutralized with acetic acid and the resulting precipitate was filtered off with suction. 1.7 g (57%) of the product were obtained.

c) (S)-4-(8-Quinolinylsulfonamido)-N-(3-phenylpropan-1-ol-2-yl)benzamide 1.5 g (4.6 mmol) of the intermediate 24b were reacted with (S)-2-amino-3-phenyl-1-propanol by the method of procedure 7a, affording 1.2 g (58%) of the product.

d) (S)-4-(8-Quinolinylsulfonamido)-N-(3-phenylpropan-1-al-2-yl)benzamide 1 g (2.2 mmol) of the intermediate was oxidized by the method of procedure 21c, affording 0.8 g of the product.

$^{1}$H-NMR (D$_{6}$-DMSO): [lacuna]=2.8(1H); 3.2(1H); 4.3 (1H); 7.0–7.3(7H); 7.5(2H); 7.7(3H); 8.2(1H); 8.4(2H); 8.7 (1H); 9.1(1H); 9.5(1H) and 10.6(1H)ppm.

Example 25

(S)-4-(2-Naphthyl)thiomethyl-N-(3-phenylpropan-1-al-2-yl)benzamide

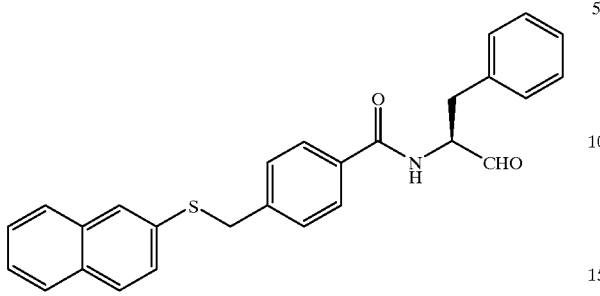

a) Methyl 4-(2-naphthylthiomethyl)benzoate 16.8 g (0.1 mol) of thionaphth-2-ole and 21.3 g (0.21 mol) of triethylamine were dissolved in 300 ml of tetrahydrofuran. At 0° C., a solution of 24 g (0.1 mol) of methyl 4-(bromomethyl)benzoate in 100 ml of tetrahydrofuran was added dropwise. The mixture was stirred for 2 h and then filtered, and the filtrate was concentrated under reduced pressure. The residue was recrystallized from n-heptane, affording 27.2 g (84%) of the product.

b) 4-(2-Naphthylthiomethyl)benzoic acid 25.9 g (42 mmol) of the intermediate 25a were hydrolyzed with 2M ethanolic sodium hydroxide solution by the method of procedure 31b. 11.9 g (96%) of the product were obtained.

c) (S)-4-(2-Naphthyl)thiomethyl-N-(3-phenylpropan-1-al-2-yl)benzamide 5.7 g (37 mmol) of (S)-2-amino-3-phenyl-1-propanol were reacted with 11 g (37 mmol) of the intermediate 25b by the method of procedure 7a. 9.5 g (60%) of the product were obtained.

d) (S)-4-(2-Naphthyl)thiomethyl-N-(3-phenylpropan-1-al-2-yl)benzamide 5 g (2.3 mmol) of the intermediate 25c were oxidized by the method of procedure 21c. 0.9 g (18%) of the product was obtained.

$^1$H-NMR($D_6$-DMSO): δ=2.9(1H); 3.3(1H); 4.4(2H); 4.5 (1H); 7.0–7.9(16H); 9.8(1H) and 10.5(1H)ppm.

Example 26

(S)-2-Phenoxy-N-(3-phenylpropan-1-al-2-yl)benzamide

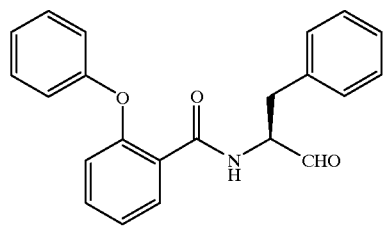

a) (S)-2-Phenoxy-N-(3-phenylpropan-1-ol-2-yl)benzamide 7.3 g (48 mmol) of (S)-2-amino-3-phenyl-1-propanol were reacted with 10.7 g (50 mmol) of 2-phenoxybenzoic acid by the method of procedure 3c. 17.3 g (100%) of the product were obtained.

(S)-2-Phenoxy-N-(3-phenylpropan-1-al-2-yl)benzamide 16.1 g (46 mmol) of the intermediate 26a were oxidized by the method of procedure 21c. 10.3 g (64%) of the product were obtained.

$^1$H-NMR($D_6$-DMSO): δ=2.9(1H); 3.2(1H); 4.5(1H); 6.7–7.7(14H); 8.4(1H) and 9.4(1H)ppm.

Example 27

(S)-4-(2-Naphthylmethyl)amido-N-(3-phenylpropan-1-al-2-yl)benzamide

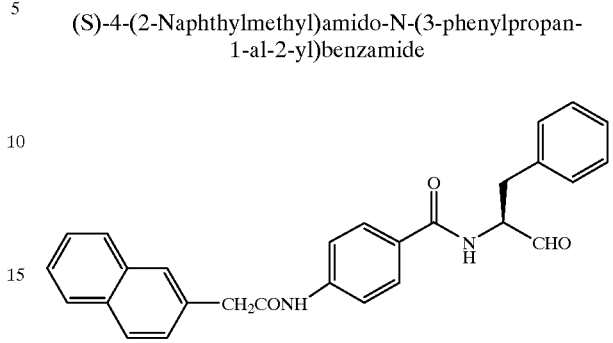

a) Ethyl 4-(2-Naphthylmethyl)amidobenzoate 10 g (53 mmol) of naphthyl acetic acid in 150 ml of anhydrous tetrahydrofuran were admixed with 9 g (56 mmol) of carbonyldiimidazole, and the mixture was heated under reflux for 1 h. 8.9 g (3 mmol) of ethyl 4-aminobenzoate were then added and the mixture was heated under reflux for a further 3 h. The mixture was then concentrated under reduced pressure. The residue was treated with 600 ml of water whereupon the product precipitated. 16.6 g (92%) of the product were obtained.

b) 4-(2-Naphthylmethyl)amidobenzoic acid 15.2 g (46 mmol) of the intermediate 27a were hydrolyzed with lithium hydroxide by the method of procedure 3b. 13.7 g (98%) of the product were obtained.

c) (S)-4-(2-Naphthylmethyl)amido-N-(3-phenylpropan-1-ol-2-yl)benzamide 10.3 g (34 mmol) of the intermediate 27b were reacted with (S)-2-amino-3-phenyl-1-propanol by the method of procedure 27a. 7.9 g (53%) of the product were obtained.

d) (S)-4-(2-Naphthylmethyl)amido-N-(3-phenylpropan-1-al-2-yl)benzamide 7.4 g (17 mmol) of the intermediate 27c were oxidized by the method of procedure 21c. 2.1 g (28%) of the product were obtained.

$^1$H-NMR ($D_6$-DMSO): δ=MS(ESI): m/e=436($M^+$).

Example 28

4-(Naphth-2-ylsulfoxymethyl)-N-((S)-3-phenylpropan-1-al-2-yl)benzamide

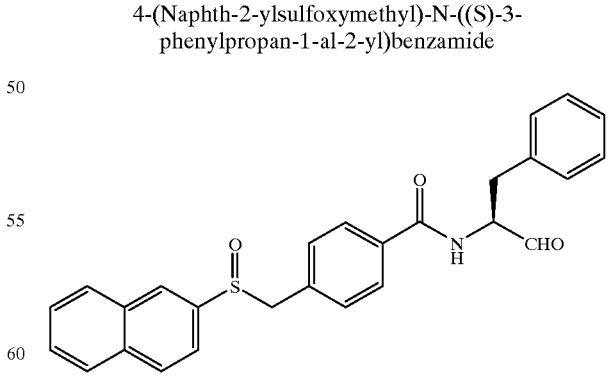

a) Methyl 4-(naphth-2-ylsulfoxymethyl)benzoate

At 0° C., 25.8 g (42 mmol) of oxone dissolved in 300 ml of water were added dropwise to 13 g (42 mmol) of the intermediate 25a in 850 ml of methanol. The mixture was stirred for about 1 h. About 1 l of water was then added and the precipitated product was filtered off with suction. 13.2 g (92%) of the product were obtained.

b) 4-(Naphth-2-ylsulfoxymethyl)benzoic acid 12.7 g (39 mmol) of the intermediate 28a were hydrolyzed with sodium hydroxide solution in ethanol/water by the method of procedure 31b. 11.5 g (94%) of the product were obtained.

c) 4-(2-Naphthyl)sulfoxymethyl-N-((S)-3-phenylpropan-1-ol-2-yl)benzamide 10.2 g (31 mmol) of the intermediate 28b were reacted with (S)-2-amino-3-phenyl-1-propanol by the method of procedure 7a. 8.7 g (61%) of the product were obtained.

d) 4-(2-Naphthyl)sulfoxymethyl-N-((S)-3-phenylpropan-1-al-2-yl)benzamide 7.46 g (17 mmol) of the intermediate 27c were oxidized by the method of procedure 21c. 4.2 g (55%) of the product were obtained.

$^1$H-NMR($D_6$-DMSO): δ=2.9(1H); 3.2(1H); 4.2(1H); 4.5 (2H); 7.0–8.1(16H); 8.8(1H) and 9.5(1H)ppm.

Example 29

(S)-4-(Naphth-2-yl)sulfonylmethyl-N-(3-phenylpropan-1-al-2-yl)benzamide

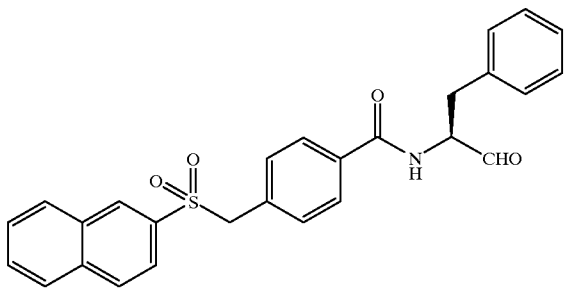

a) (S)-4-(Naphth-2-yl )sulfonylmethyl-N-(phenylpropan-1-ol-2-yl)benzamide

With cooling, 5.1 g of 55% strength (16.1 mmol) 3-chloroperbenzoic acid were added a little at a time to 3.45 g (8.1 mmol) of (S)-4-naphthyl-2-thiomethyl-N-(3-phenylpropan-1-al-2-yl)benzamide (intermediate 25c) in 500 ml of methylene chloride. The mixture was stirred at room temperature for 16 [lacuna]. The reaction solution was then washed three times with 20% strength aqueous sodium sulfite solution. The organic phase was dried and concentrated under reduced pressure. 0.5 g (14%) of the product was obtained.

b) (S)-4-(Naphth-2-yl)sulfonylmethyl-N-(3-phenylpropan-1-al-2-yl)benzamide 0.4 g (0.9 mmol) of the intermediate 29a was oxidized by the method of procedure 21c. 0.36 g (88%) of the product was obtained.

$^1$H-NMR($D_6$-DMSO): δ=2.9(1H); 3.3(1H); 4.5(1H); 4.9 (2H); 7.0–7.3(6H); 7.5–7,9(5H); 8-0–8.3(4H); 8.4(1H); 8.8 (1H) and 9.5(1H)ppm.

Example 30

(S)-2-Phenyl-N-(3-phenylpropan-1-al-2-yl)benzamide

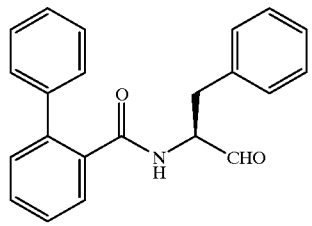

a) (S)-2-Phenyl-N-(3-phenylpropan-1-ol-2-yl)benzamide 2 g (10 mmol) of 2-phenylbenzoic acid were reacted with (S)-2-amino-3-phenyl-1-propanol by the method of procedure 3a, affording 2.1 g (64%) of the product.

b) (S)-2-Phenyl-N-(3-phenylpropan-1-al-2-yl)benzamide 1.0 g (3 mmol) of the intermediate 30a was oxidized by the method of procedure 21c. 0.4 g (40%) of the product was obtained.

$^1$H-NMR(CDCl$_3$): δ=2.9(1H); 3.0(1H); 4.7(1H); 5.9(1H); 6.9–7.7(14H) and 9.4(1H)ppm.

Example 31

(S)-2-(E-2-(Naphth-2-yl)-ethen-1-yl)-N-(3-phenylpropan-1-al-2-yl)benzamide

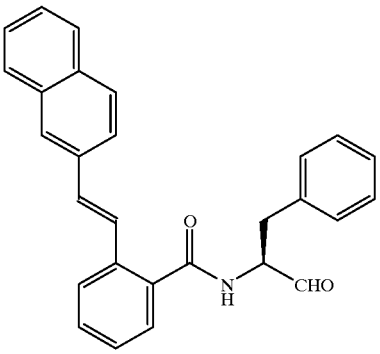

a) Ethyl 2-(E-2-(naphth-2-yl)-ethen-1-yl)benzoate 29.7 g (0.13 mol) of 2-vinylnaphthalene, 25 g (0.16 mol) of ethyl 2-bromobenzoate, 22.5 ml (0.16 mol) of triethylamine, 0.54 g of palladium diacetate and 1.44 g of triphenylphosphine in 200 ml of acetonitrile were heated to 100° C. for 20 h. The reaction mixture was then poured into water and the mixture was extracted repeatedly with ethyl acetate. The organic phase was concentrated under reduced pressure and the residue was purified chromatographically on silica gel. 34 g (71%) of the product were obtained.

b) 2-(E-2-(Naphth-2-yl)-ethen-1-yl)benzoic acid 34 g (112.5 mmol) of the intermediate 31a were dissolved in 200 ml of tetrahydrofuran and treated with 9.5 g (168.7 mmol) of 80% strength potassium hydroxide dissolved in 150 ml of water. The reaction mixture was heated under reflux for 10 h. The reaction mixture was then acidified with concentrated hydrochloric acid and extracted with ethyl acetate. The organic phase was washed with water, dried and concentrated under reduced pressure. The residue was treated with a little ethyl acetate and filtered off with suction. 23.8 g (78%) of the product were obtained.

c) (S)-2-(E-2-(Naphth-2-yl)-ethen-1-yl)-N-(3-phenylpropan-1-ol-2-yl)benzamide 1 g (3.6 mmol) of the intermediate 31b and 0.55 g (3.6 mmol) of (S)-2-amino-3-phenyl-1-propanol were reacted by the method of procedure 3c. 1.1 g (75%) of the product were obtained.

d) (S)-2-(E-2-(Naphth-2-yl)-ethen-1-yl)-N-(3-phenylpropan-1-al-2-yl)benzamide 0.9 g (2.2 mmol) of the intermediate 31c was oxidized by the method of procedure 21c. 0.57 g (66%) of the product was obtained.

MS(ESI): m/e=405 (M+).

Example 32

(S)-2-(E-2-(3,4-Dimethoxyphenyl)-ethen-1-yl)-N-(3-phenylpropan-1-al-2-yl)benzamide

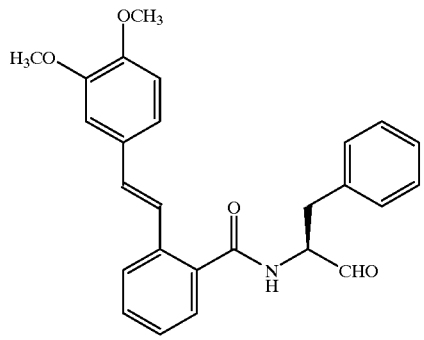

a) Ethyl 2-(E-2-(3,4-Dimethoxyphenyl)-ethen-1-yl) benzoate 5 g (30.5 mmol) of 3,4-dimethoxystyrene were reacted with ethyl 2-bromobenzoate in dimethylformamide at 120° C. by the method of procedure 31a. 1.2 g (4%) [sic] of the product were obtained.

b) 2-(E-2-(3,4-Dimethoxyphenyl)-ethen-1-yl)benzoic acid 7 g (22 mmol) of the intermediate 32a were hydrolyzed with 4M aqueous sodium hydroxide solution by the method of procedure 31b. 6.2 g (98%) of the product were obtained.

c) (S)-2-(2-(3,4-Dimethoxyphenyl)-ethen-1-yl)-N-(3-phenylpropan-1-ol-2-yl)benzamide 1 g (3.5 mmol) of the intermediate 32b was reacted with (S)-2-amino-3-phenyl-1-propanol by the method of procedure 7a. 1.3 g (90%) of the product were obtained.

d) (S)-2-(E-2-(3,4-Dimethoxyphenyl)-ethen-1-yl)-N-(3-phenylpropan-1-al-2-yl)benzamide 1 g (2.4 mmol) of the intermediate 32c was oxidized by the method of procedure 21c. 1 g (100%) of the product was obtained.

$^1$H-NMR(D$_6$-DMSO): δ=2.9(1H); 3.2(1H); 3.8(6H); 4.5 (1H); 6.9–7.6(12H); 7.8(2H); 8.8(1H) and 9.7(1H)ppm.

Example 33

(S)-6-Methyl-3-(2-naphthyl)amido-N-(3-phenylpropan-1-al-2-yl)benzamide

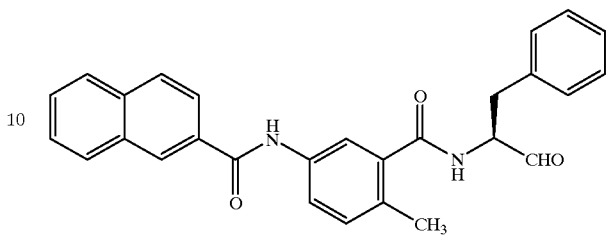

a) (S)-2-Methyl-N-(3-phenylpropan-1-ol-2-yl)-5-nitrobenzamide 5 g (27.6 mmol) of 2-methyl-5-nitrobenzoic acid were reacted with 4.2 g (27.6 mmol) of (S)-2-amino-3-phenyl-1-propanol by the method of procedure 3c. 7.5 g (87%) of the product were obtained.

b) (S)-5-Amino-2-methyl-N-(3-phenylpropan-1-ol-2-yl) benzamide 6.3 g (20 mmol) of the intermediate 33a were dissolved in 150 ml of ethanol and hydrogenated after the addition of 0.5 g of palladium/carbon (10%). The mixture was then filtered and the filtrate was concentrated under reduced pressure. 4.9 g of the product were obtained.

c) (S)-6-Methyl-3-(2-naphthyl)amido-N-(3-phenylpropan-1-ol-2-yl)benzamide 1 g (3.5 mmol) of the intermediate 33b was reacted with 2-naphthoyl chloride by the method of procedure 3a. 1.2 g (78%) of the product were obtained.

d) (S)-6-Methyl-3-(2-naphthyl)amido-N-(3-phenylpropan-1-al-2-yl)benzamide 1 g (2.3 mmol) of the intermediate 33c was oxidized by the method of procedure 21c. 1.0 g (100%) of the product was obtained.

$^1$H-NMR(D$_6$-DMSO): δ=2.2(3H); 2.8(1H); 3.3(1H); 4.5 (1H); 7.0–8.2(13H); 8.6(2H); 8.8(1H); 7.7(1H) and 10.5 (1H)ppm.

Example 34

(S)-3-Methyl-4-(2-naphthyl)amido-N-(3-phenylpropan-1-al-2-yl)-benzamide

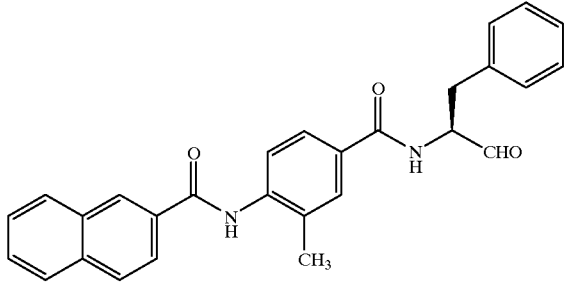

a) (S)-3-Methyl-N-(3-phenylpropan-1-ol-2-yl)-4-nitrobenzamide 5 g (27.6 mmol) of 3-methyl-4-nitrobenzoic acid were reacted with 4.2 g (27.6 mmol) of (S)-2-amino-3-phenyl-1-propanol by the method of procedure 3c. 7.1 g (82%) of the product were obtained.

b) (S)-4-Amino-3-methyl-N-(3-phenylpropan-1-ol-2-yl)benzamide 7 g (22.3 mmol) of the intermediate 34a were hydrogenated by the method of procedure 33b. 5.6 g (89%) of the product were obtained.

c) (S)-3-Methyl-4-(2-naphthyl)amido-N-(3-phenylpropan-1-ol-2-yl)benzamide 1 g (3.5 mmol) of the intermediate 34b was reacted with 2-naphthoyl chloride by the method of procedure 3a. 1.3 g (83%) of the product were obtained.

d) (S)-3-Methyl-4-(2-naphthyl)amido-N-(3-phenylpropan-1-al-2-yl)benzamide 1 g (2.3 mmol) of the intermediate 34c was oxidized by the method of procedure 21c. 0.95 g (96%) of the product was obtained.

MS(ESI): m/E=436(M$^+$).

Example 35

(S)-4-Phenylsulfonamido-N-(3-phenylpropan-1-al-2-yl)benzamide

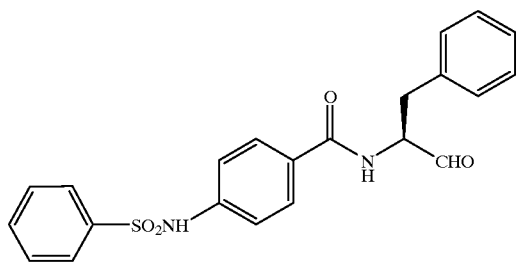

a) Ethyl 4-phenylsulfonamidobenzoate 5 g (30.3 mmol) of ethyl 4-aminobenzoate were dissolved in 100 ml of pyridine and admixed dropwise at 0° C. with 4.1 ml (31.8 mmol) of benzenesulfonyl chloride. The mixture was stirred for 3 h. The mixture was then concentrated under reduced pressure and the residue was recrystallized from ethanol. 7.3 g (85%) of the product were obtained.

b) 4-Phenylsulfonamidobenzoic acid 7 g (22.9 mmol) of the intermediate 35a were hydrolyzed under reflux with 4M aqueous sodium hydroxide solution by the method of procedure 31b. 5.9 g (94%) of the product were obtained.

c) (S)-4-Phenylsulfonamido-N-(3-phenylpropan-1-ol-2-yl)benzamide 2 g (7.2 mmol) of the intermediate 35b were reacted with (S)-2-amino-3-phenyl-1-propanol by the method of procedure 7a. 1.9 g (65%) of the product were obtained.

d) (S)-4-Phenylsulfonamido-N-(3-phenylpropan-1-al-2-yl)benzamide 1 g (2.4 mmol) of the intermediate 35c was oxidized by the method of procedure 21c. 0.9 g (94%) of the product was obtained.

$^1$H-NMR(D$_6$-DMSO): =2.8(1H); 3.2(1H); 4.3(1H); 7.0–7.9(14H); 8.7(1H); 9.5(1H) and 10.6(1H)ppm.

Example 36

(S)-2-Methyl-5-(2-naphthyl)sulfonamido-N-(3-phenylpropan-1-al-2-yl)benzamide

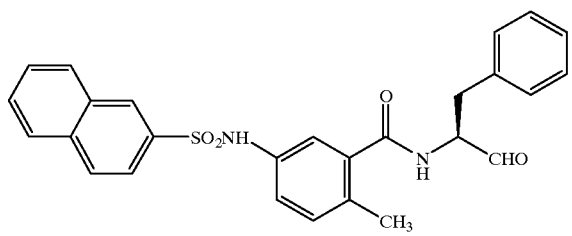

a) 2-Methyl-N-(3-phenylpropan-1-ol-2-yl)-5-nitrobenzamide 5 g (27.6 mmol) of 2-methyl-5-nitrobenzoic acid were reacted with (S)-2-amino-3-phenyl-1-propanol by the method of procedure 3c. 7.5 g (87%) of the product were obtained.

b) 5-Amino-2-methyl-N-(3-phenylpropan-1-ol-2-yl)benzamide 6.3 g (20.4 mmol) of the intermediate 36a were hydrogenated by the method of procedure 33b. 4.9 g (86%) of the product were obtained.

c) (S)-2-Methyl-5-(2-naphthyl)sulfonamido-N-(3-phenylpropan-1-ol-2-yl)benzamide 1 g (3.5 mmol) of the intermediate 36b was reacted with 2-naphthoyl chloride by the method of procedure 4b. 1.2 g (73%) of the product were obtained.

d) (S)-2-Methyl-5-(2-naphthyl)sulfonamido-N-(3-phenylpropan-1-al-2-yl)benzamide 1 g (2.1 mmol) of the intermediate 36c was oxidized by the method of procedure 21c. 0.65 g (66%) of the product was obtained.

$^1$H-NMR(D$_6$-DMSO): δ=2.0(3H); 2.8(1H); 3.2(1H); 4.5 (1H); 6.9–7.5(8H); 7.6–7.9(3H); 7.9–8.2(3H); 8.3(1H); 8,5 (1H); 9.5(1H) and 10.3(1H)ppm.

Example 37

(S)-4-Methyl-3-(2-naphthyl)sulfonamido-N-(3-phenylpropan-1-al-2-yl)benzamide

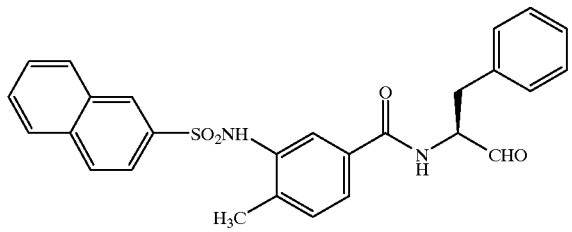

a) 3-Methyl-N-(3-phenylpropan-1-ol-2-yl)-4-nitrobenzamide 5 g (27.6 mmol) of 3-methyl-4-nitrobenzoic acid were reacted with (S)-2-amino-3-phenyl-1-propanol by the method of procedure 3c. 7.1 g (82%) of the product were obtained.

b) 4-Amino-3-methyl-N-(3-phenylpropan-1-ol-2-yl)benzamide 7 g (22.3 mmol) of the intermediate 37a were hydrogenated by the method of procedure 33b. 5.6 g (89%) of the product were obtained.

c) (S)-4-Methyl-3-(2-naphthyl)sulfonamido-N-(3-phenylpropan-1-ol-2-yl)benzamide 1.5 g (5.3 mmol) of the intermediate 37b were reacted with 2-naphthoyl chloride by the method of procedure 35a. 1.4 g (56%) of the product were obtained.

d) (S)-4-Methyl-3-(2-naphthyl)sulfonamido-N-(3-phenylpropan-1-al-2-yl)benzamide 1.1 g (2.3 mmol) of the intermediate 37c were oxidized by the method of procedure 21c. 1.0 g (92%) of the product was obtained.

$^1$H-NMR(D$_6$-DMSO): δ=2.1(3H); 2.9(1H); 3.2(1H); 4.3 (1H); 7.0–8.2(13H); 8.2(2H); 8.7(1H); 9.5(1H) and 9.8(1H) ppm.

Example 38

(S)-6-Methyl-3-phenylsulfonamido-N-(3-phenylpropan-1-al-2-yl)benzamide

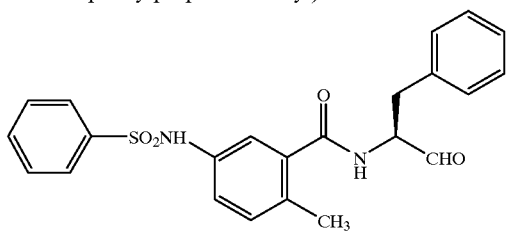

a) (S)-6-Methyl-3-phenylsulfonamido-N-(3-phenylpropan-1-ol-2-yl)benzamide 1 g (3.5 mmol) of the intermediate 36b was reacted with benzenesulfonyl chloride by the method of procedure 35a. 1.2 g (83%) of the product were obtained.

b) (S)-6-Methyl-3-phenylsulfonamido-N-(3-phenylpropan-1-al-2-yl)benzamide 1 g (2.4 mmol) of the intermediate 38c was oxidized by the method of procedure 21c. 0.8 g of the product was obtained.

$^1$H-NMR(D$_6$-DMSO): δ=2.0(3H); 2.8(1H); 3.2(1H); 4.4 (1H); 6.9–7.8(13H); 8.6(1H); 9.5(1H) and 10.2(1H)ppm.

Example 39

(S)-3-Phenylsulfonamido-N-(3-phenylpropan-1-al-2-yl)benzamide

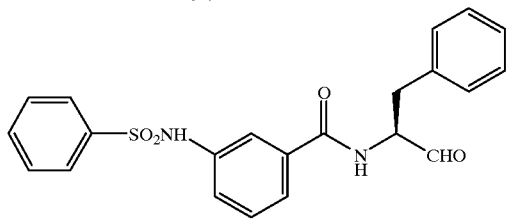

a) (S)-N-(3-phenylpropan-1-ol-2-yl)-4-nitrobenzamide 5 g (33 mmol) of (S)-2-amino-3-phenyl-1-propanol were reacted with 6.1 g (33 mmol) of 3-nitrobenzoyl chloride by the method of procedure 10a. 9.2 g (93%) of the product were obtained.

b) (S)-4-Amino-N-(3-phenylpropan-1-ol-2-yl)benzamide 9.1 g (30.3 mmol) of the intermediate 39a were hydrogenated by the method of procedure 33b. 8.4 g (100%) of the product were obtained.

c) (S)-3-Phenylsulfonamido-N-(3-phenylpropan-1-ol-2-yl)benzamide 1 g (3.7 mmol) of the intermediate 39b was reacted with benzenesulfonyl chloride by the method of procedure 35a. 0.72 g (48%) of the product was obtained.

d) (S)-3-Phenylsulfonamido-N-(3-phenylpropan-1-al-2-yl)benzamide 0.6 g (1.5 mmol) of the intermediate 39c was oxidized by the method of procedure 21c. 0.55 g (93%) of the product was obtained.

MS: m/e=408(M$^+$).

Example 40

(S)-4-(E-2-Naphtho-2-yl-1-ethenyl)-N-(3-phenylpropan-1-al-2-yl)benzamide

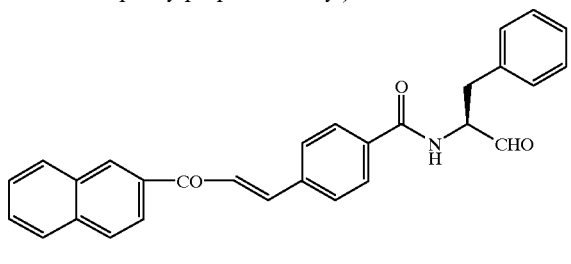

a) 4-(E-2-Naphtho-2-yl-1-ethenyl)benzoic acid 4.5 g (26.4 mmol) of 2-acetylnaphthalene and 4.3 g (26.4 [lacuna]) of methyl 4-formylbenzoate were dissolved in 100 ml of methanol and treated with 16 ml of 4M aqueous sodium hydroxide solution. The mixture was stirred for about 1 h. A large volume of water was then added and the mixture was stirred for a further 72 h. The mixture was then acidified with concentrated hydrochloric acid whereupon a precipitate formed. The precipitate was filtered off with suction and recrystallized from ethanol. 7.2 g (90%) of the product were obtained.

b) (S)-4-(E-2-Naphtho-2-yl-1-ethenyl)-N-(-3-phenylpropan-1-ol-2-yl)benzamide 1.2 g (7.6 mmol) of (s)-2-amino-3-phenyl-1-propanol were reacted with 2.3 g (7.6 mmol) of the intermediate 40a by the method of procedure 7a. 2.1 g (64%) of the product were obtained.

(S)-4-(E-2-Naphtho-2-yl-1-ethenyl)-N-(3-phenylpropan-1-al-2-yl)benzamide 0.7 g (1.65 mmol) of the intermediate 40b was oxidized by the method of procedure 21c. 0.66 g (92%) of the product was obtained.

MS: m/e=433(M$^+$).

Example 41

(S)-3-(E-2-Naphtho-2-yl-1-ethenyl)-N-(3-phenylpropan-1-al-2-yl)benzamide

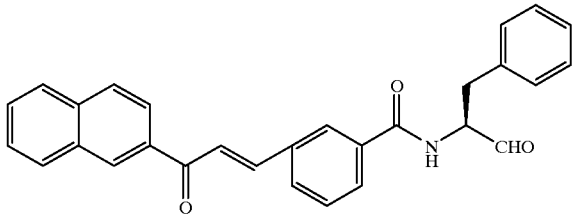

a) 4-(E-2-Naphtho-2-yl-1-ethenyl)benzoic acid 4.5 g (26.4 mmol) of 2-acetylnaphthalene were reacted with 4 g (26.4 mmol) of 3-formylbenzoic acid by the method of procedure 40a. 7.4 g (93%) of the product were obtained.

b) (S)-3-(E-2-Naphtho-2-yl-1-ethenyl)-N-(3-phenylpropan-1-ol-2-yl)benzamide 0.6 g (4 mmol) of (S)-2-amino-3-phenyl-1-propanol was reacted with 1.2 g (4 mmol) of the intermediate 41a by the method of procedure 7a. 1.5 g (87%) of the product were obtained.

c) (S)-3-(E-2-Naphtho-2-yl-1-ethenyl)-N-(3-phenylpropan-1-al-2-yl)benzamide 1 g (2.3 mmol) of the intermediate 41b was oxidized by the method of procedure 21c. 0.91 g of the product was obtained.

MS: m/e=433(M+).

Example 42

(S)-N-(4-Methylthio-1-butanal-2-yl)-3-(2-naphthylsulfonamido)benzamide

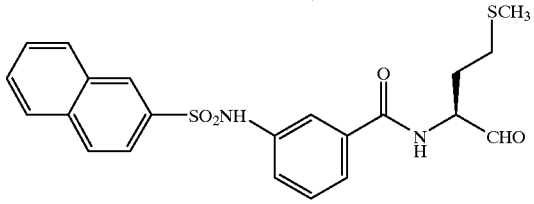

a) (S)-N-(4-Methylthio-1-butanol-2-yl)-3-(2-naphthylsulfonamido)benzamide 2 g (3.1 mmol) of 3-(2-naphthylsulfonamido)benzoic acid (intermediate 22a) were reacted with (S)-2-amino-4-methylthio-1-butanol by the method of procedure 7a, affording 1.6 g (59%) of the product.

b) (S)-N-(4-Methylthio-1-butanol-2-yl)-3-(2-naphthylsulfonamido)benzamide 1.0 g (2.5 mmol) of the intermediate 42a was oxidized by the method of procedure 21c. 0.74 g (75%) of the product was obtained.

MS: m/e=442(M+).

Example 43

(S)-4-(2-Naphthyl)amido-2-(E-2-phenylethen-1-yl)-N-(3-phenylpropan-1-al-2-yl)benzamide

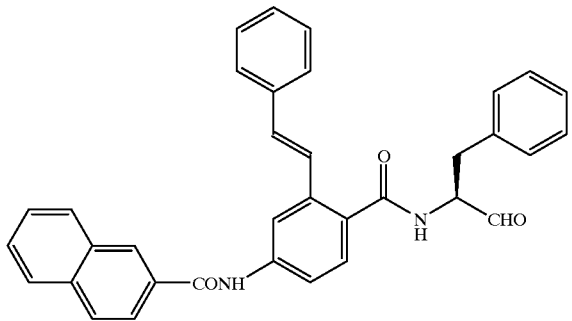

a) 2-Bromo-4-nitro-benzoic acid 75 g (0.35 mol) of 2-bromo-4-nitrotoluene, 12 ml of aliquot 336 and 39 g (0.47 mol) of sodium hydrogen sulfate in 1.5 l of water were heated to 80° C. The mixture was stirred well and 183 g (1.16 mol) of potassium permanganate were then added a little at a time. The mixture was then heated under reflux for 45 min. The mixture was filtered through CELITE and the filtrate was concentrated to about 700 ml under reduced pressure. The aqueous solution was acidified with concentrated hydrochloric acid, whereupon the product precipitated. 45 g (53%) of the product were obtained.

b) Ethyl 2-bromo-4-nitro-benzoate 44.5 g (0.18 mol) of the intermediate 43a were added to 450 ml of ethanol and treated carefully with 45 ml of concentrated sulfuric acid. The mixture was then heated under reflux for 4 h. The mixture was then poured into ice-water and the product was extracted with ethyl acetate. The organic phase was washed with aqueous sodium hydrogen sulfate solution and water, dried and concentrated under reduced pressure. 50.4 g (100%) of the product were obtained.

c) Ethyl 4-nitro-2-(E-2-phenylethen-1-yl)benzoate 50 g (0.18 mol) of the intermediate 43b were reacted with styrene in dimethylformamide at reflux temperature by the method of procedure 31a. 35 g (65%) of the product were obtained.

d) 4-Nitro-2-(E-2-phenylethen-1-yl)benzoic acid 35 g (0.12 mol) of the intermediate 43c were hydrolyzed with aqueous sodium hydroxide solution by the method of procedure 31b. 29 g (92%) of the product were obtained.

e) (S)-4-Nitro-2-(E-2-phenylethen-1-yl)-N-(3-phenylpropan-1-ol-2-yl)benzamide 5.6 g (37.1 mmol) of (S)-2-amino-3-phenyl-1-propanol were reacted with 10 g (37.1 mmol) of the intermediate 43d by the method of procedure 7a. 11.3 g (76%) of the product were obtained.

f) (S)-4-Amino-2-(E-2-phenylethen-1-yl)-N-(3-phenylpropan-1-ol-2-yl)benzamide 10 g (24.9 mmol) of the intermediate 43e were hydrogenated in 200 ml of tetrahydrofuran in the presence of 3 g of Raney nickel. The mixture was then filtered and the filtrate was concentrated under reduced pressure. Recrystallization from ethanol gave 6.2 g (69%) of the product.

g) (S)-4-(2-Naphthyl)amido-2-(E-2-phenylethen-1-yl)-N-(3-phenylpropan-1-ol-2-yl)benzamide 1 g (2.7 mmol) of the intermediate 43f was reacted with 2-naphthoyl chloride by the method of procedure 10a. 1.2 g (86%) of the product were obtained.

h) (S)-4-(2-Naphthyl)amido-2-(E-2-phenylethen-1-yl)-N-(3-phenylpropan-1-al-2-yl)benzamide 1.0 g (1.9 mmol) of the intermediate 43 g was oxidized by the method of procedure 21c. 0.75 g (76%) of the product was obtained.

MS: m/e=524(M+).

Example 44

(S)-3-(2-Naphthyl)sulfonylamido-N-(pentan-1-al-2-yl)benzamide

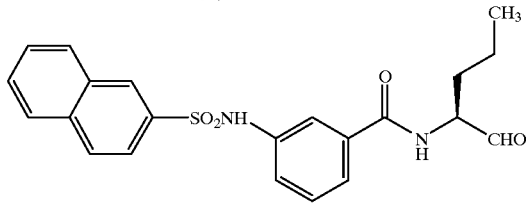

a) (S)-3-(2-Naphthyl)sulfonylamido-N-(pentan-1-ol-2-yl)benzamide 2 g (6.1 mmol) of 3(2-naphthylsulfonamido)benzoic acid (intermediate 22a) were reacted with D,L-2-amino-1-pentanol by the method of procedure 7a, affording 1.9 g (76%) of the product.

b) (S)-3-(2-Naphthyl)sulfonylamido-N-(pentan-1-al-2-yl)benzamide 1.3 g (3.2 mmol) of the intermediate 44a were oxidized by the method of procedure 21c. 1.3 g (100%) of the product were obtained.

$^1$H-NMR(D$_6$-DMSO): δ=0.9(3H); 1.1–1.9(4H); 4.1(1H); 7.1–8.1(10H); 8.3(1H); 8.6(1H); 9.4(1H) and 10.5(1H)ppm.

Example 45

3-(2-Naphthyl) sulfonylamido-N-(butan-1-al-2-yl)benzamide

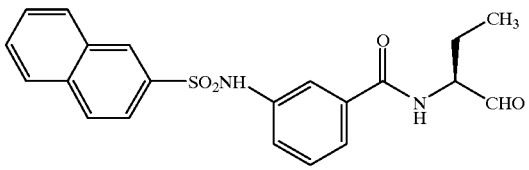

a) 3-(2-Naphthyl)sulfonylamido-N-(butan-1-ol-2-yl)benzamide 2 g (6.1 mmol) of 3-(2-naphthylsulfonamido)benzoic acid (intermediate 22a) were reacted with D,L-2-amino-1-butanol by the method of procedure 7a, affording 1.3 g (54%) of the product.

b) 3-(2-Naphthyl)sulfonylamido-N-(butan-1-al-2-yl)benzamide 1 g (2.5 mmol) of the intermediate 45a was oxidized by the method of procedure 21c. 0.55 g of the product was obtained.

$^1$H-NMR($D_6$-DMSO): δ=1.0(3H); 1.7(1H); 1.9(1H); 4.1(1H); 7.1–8.1(9H); 8.3(2H); 8.6(1H); 9.5(1H) and 10.6(1H) ppm.

Example 46

3-(2-Naphthyl)sulfonamido-N-(3-indol-3-ylpropan-1-al-2-yl)benzamide

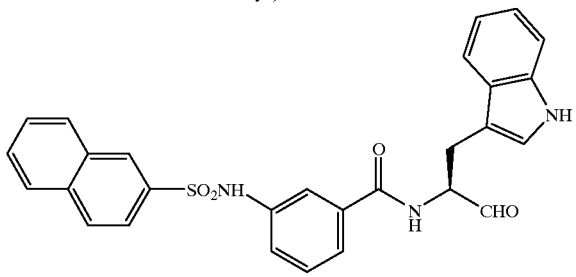

a) 3-(2-Naphthyl)sulfonamido-N-(3-indol-3-ylpropan-1-ol-2-yl)benzamide 1 g (3.1 mmol) of 3(2-naphthylsulfonamido)benzoic acid (intermediate 22a) was reacted with D,L-3-indol-3-ylpropan-1-ol by the method of procedure 7a, affording 0.9 g (60%) of the product.

b) 3-(2-Naphthyl)sulfonamido-N-(3-indol-3-ylpropan-1-al-2-yl)benzamide 0.8 g (1.6 mmol) of the intermediate 46a was oxidized by the method of procedure 21c. 0.71 g (90%) of the product was obtained.

MS: m/e=497(M$^+$).

Example 47

(S)-N-(3-Cyclohexylpropan-1-al-2-yl)-3-(2-naphthyl)sulfonamidobenzamide

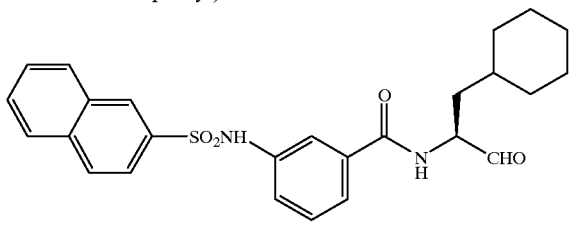

a) (S)-N-(3-Cyclohexylpropan-1-al-2-yl)-3-(2-naphthyl)sulfonamidobenzamide 1.5 g (4.6 mmol) of 3-(2-naphthylsulfonamido)benzoic acid (intermediate 22a) were reacted with (S)-2-amino-3-cyclohexylpropan-1-ol by the method of procedure 7a, affording 1.8 g (77%) of the product.

b) (S)-N-(3-Cyclohexylpropan-1-al-2-yl)-3-(2-naphthyl)sulfonamidobenzamide 1.4 g (3 mmol) of the intermediate 47a were oxidized by the method of procedure 21c. 1.35 g (100%) of the product were obtained.

$^1$H-NMR($D_6$-DMSO): δ=0.8–1.9(13H); 4.2(1H); 7.0–8.1(10H); 8.2(1H); 8.6(1H); 9.3(1H) and 10.5(1H)ppm.

Example 48

(S)-4-Nitro-2(E-phenyl-1-ethenyl)-N(3-phenylpropan-1-al-2-yl)benzamide [sic]

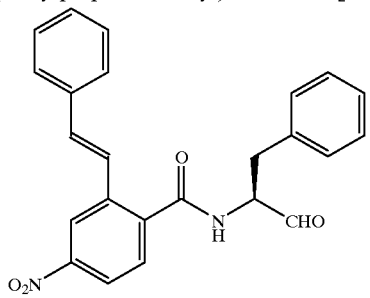

0.4 g (1 mmol) of (S)-4-nitro-2-(E-2-phenylethen-1-yl)-N-(3-phenylpropan-1-ol-2-yl)benzamide (intermediate 43e) was oxidized by the method of procedure 21c. 0.35 g (88%) of the product was obtained.

MS: m/e=(M$^+$) [sic].

Example 49

(S)-4-(2-Naphthylsulfonamido)methyl-N-(3-phenylpropan-1-al-2-yl)benzamide

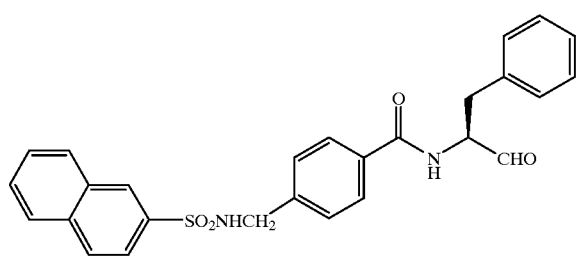

a) 4-(2-Naphthylsulfonamido)methylbenzoic acid 3.8 g (25 mmol) of 4-(aminomethyl)benzoic acid were reacted with 2-naphthalenesulfonyl chloride by the method of procedure 4b, affording 6.1 g (72%) of the product.

b) (S)-4-(2-Naphthylsulfonamido)methyl-N-(3-phenylpropan-1-ol-2-yl)benzamide 3.1 g (9 mmol) of the intermediate 49a were reacted with (S)-2-amino-3-cyclohexylpropan-1-ol by the method of procedure 7a, affording 2.4 g (62%) of the product.

c) (S)-4-(2-Naphthylsulfonamido)methyl-N-(3-phenylpropan-1-al-2-yl)benzamide 1.6 g (3.6 mmol) of the intermediate 49b were oxidized by the method of procedure 21c. 1.0 g (64%) of the product was obtained.

$^1$H-NMR($D_6$-DMSO): δ=2.9(1H); 3.3(1H); 4.02H); 4.5(1H); 7.0–8.5(17H); 8.8(1H) and 9.5(1H)ppm.

Example 50

(S)-6-Bromo-3-(2-naphthyl)sulfonylamido-N-(3-phenylpropan-1-al-2-yl)benzamide

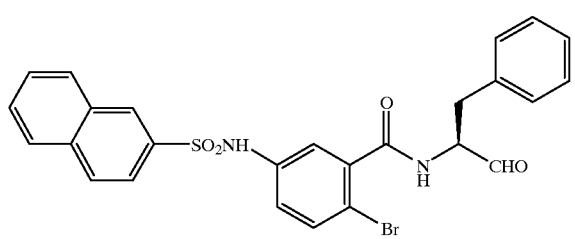

a) Ethyl 2-bromo-5-nitrobenzoate 22.9 g (0.1 mol) of ethyl 2-bromobenzoate were carefully introduced into 55 ml of sulfuric acid. At 0° C., 16.5 ml of nitrating acid (prepared at 0° C. from 5.5 ml of 98% strength nitric acid and 11 ml of 97% strength sulfuric acid) were subsequently added dropwise and the mixture was stirred for about 1 h. The reaction mixture was then carefully poured into ice-water. The precipitate was recrystallized from ethanol, yielding 17.7 g (64%) of the product.

b) Ethyl 5-amino-2-bromobenzoate 10 g (36 mmol) of the intermediate 50a were dissolved in 200 ml of glacial acetic acid and heated to 80° C. 12 g (21.5 mmol) of iron powder were then carefully (violent reaction) added a little at a time. The precipitate that formed was filtered off with suction and the filtrate was concentrated under reduced pressure. This residue was acidified with hydrochloric acid and extracted with ethyl acetate. The organic phase was dried and concentrated under reduced pressure. 6 g (68%) of the product were obtained.

c) Ethyl 6-bromo-3-(2-naphthyl)sulfonylamidobenzoate 5.5 g (22.5 mmol) of the intermediate 50b were reacted with 2-naphthylsulfonyl chloride by the method of procedure 4b. After chromatographic purification (eluent: toluene/ethanol=17/3), 7 g (72%) of the product were obtained.

d) 6-Bromo-3-(2-naphthyl)sulfonylamidobenzoic acid 3 g (6.9 mmol) of the intermediate 50c were hydrolyzed by the method of procedure 3b. 2.5 g (89%) of the product were obtained.

e) (S)-6-Bromo-3-(2-naphthyl)sulfonylamido-N-(3-phenylpropan-1-ol-2-yl)benzamide 1 g (2.5 mmol) of the intermediate 50d was reacted with (S)-2-amino-3-phenylpropan-1-ol by the method of procedure 7a, affording 0.87 g (87%) of the product after chromatographic purification (eluent: ethyl acetate/n-heptane=2/1).

f) (S)-6-Bromo-3-(2-naphthyl)sulfonylamido-N-(3-phenylpropan-1-al-2-yl)benzamide 0.72 g (1.3 mmol) of the intermediate 50e was oxidized by the method of procedure 21c. 0.6 g (86%) of the product was obtained.

$^1$H-NMR(D$_6$-DMSO): δ=2.8(1H); 3.2(1H); 4.5(1H); 7.0–8.1(12H); 8.4(1H); 8.9(1H); 9.6(1H) and 10.8(1H) ppm.

Example 51

(S)-4-(2-Naphthyl)sulfonamido-N-(3-phenylpropan-1-al-2-yl)benzamide

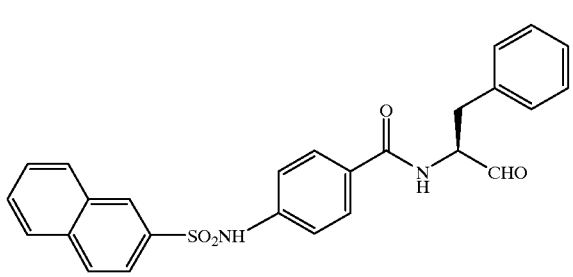

a) Ethyl 4-(2-naphthylsulfonamido)benzoate 10 g (60.5 mmol) of ethyl 4-aminobenzoate and 13.7 g (60.5 mmol) of 2-naphthylsulfonyl chloride were reacted by the method of procedure 4b, affording 13.6 g (64%) of the product.

b) 4-(2-Naphthylsulfonamido)benzoic acid 13.2 g (37.1 mmol) of the intermediate 51a were hydrolyzed with lithium hydroxide by the method of procedure 3b. 11.1 g (95%) of the product were obtained.

c) (S)-4-(2-Naphthyl)sulfonamido-N-(3-phenylpropan-1-ol-2-yl)benzamide 1.5 g (4.6 mmol) of the intermediate 51b were reacted with (S)-2-amino-3-phenyl-1-propanol by the method of procedure 7a, affording 1.7 g (81%) of the product.

d) (S)-3-(2-Naphthyl)sulfonamido-N-(3-phenylpropan-1-al-2-yl)benzamide 1.4 g (3 mmol) of the intermediate 22b were oxidized with dimeth [sic] sulfoxide/trifluoroacetic anhydride by the method of procedure 1c. After chromatographic purification (eluent: toluene/acetone=1/1), 0.12 g of the product was obtained.

$^1$H-NMR(D$_6$-DMSO): δ=2.9(1H); 3.2(1H); 4.3(1H); 7.0–8.1(14H); 8.4(2H); 8.6(1H); 9.5(1H) and 11.7(1H)ppm.

Example 52

(S)-2-(2-Naphthylmethyl)-N-(3-phenylpropan-1-al-2-yl)benzamide

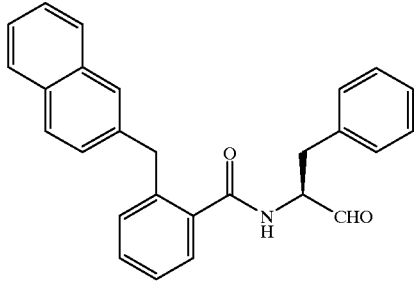

a) 4,4-Dimethyl-2-(2-(naphth-2-yl-hydroxymethyl)phenyl)-2-oxazolin

At −78° C., 104 ml of a 1.6M solution of butyl lithium were slowly added dropwise to 25 g (0.14 mol) of 4,4-dimethyl-2-phenyl-2-oxazolin and 0.1 g of triphenylmethane in 400 ml of anhydrous tetrahydrofuran. The mixture was stirred for 1 h. The mixture was then allowed to warm to −30° C. and a solution of 20.3 g (0.13 mol) of 2-naphthaldehyde in 200 ml of anhydrous tetrahydrofuran was added dropwise. Stirring was continued for about 1 h at −20 to −30° C. The reaction solution was then allowed to warm to room temperature and the solvent was removed under reduced pressure. The residue was introduced into ice-water which was then extracted with ether. The organic phase was dried and concentrated under reduced pressure. This residue was purified chromatographically (eluent: n-heptane/acetone=40/3), affording 25.3 g (54%) of the product.

b) 3-Napth-2-ylphthalide 22 g (66 mmol) of the intermediate 52a were heated under reflux in a mixture of 250 ml of ethanol and 100 ml of 1M hydrochloric acid for 2 h. The ethanol was then removed under reduced pressure and the resulting precipitate was filtered off with suction. 16.4 g (95%) of the product were obtained.

c) 2-Naphth-2-yl-benzoic acid 16 g (61.5 mmol) of the intermediate 52b were dissolved in a mixture of 100 ml of tetrahydrofuran and 250 ml of ethanol and hydrogenated after the addition of 5 g of palladium/barium sulfate. The mixture was then filtered and the filtrate was concentrated under reduced pressure. The residue was recrystallized from toluene, affording 13.6 g (85%) of the product.

d) (S)-2-(2-Naphthylmethyl)-N-(3-phenylpropan-1-ol-2-yl) benzamide 1 g (3.8 mmol) of the intermediate 51c was reacted with (S)-2-amino-3-phenyl-1-propanol by the method of procedure 7a, affording 1.2 g (80%) of the product.

e) (S)-2-(2-Naphthylmethyl)-N-(3-phenylpropan-1-al-2-yl) benzamide 1 g (2.5 mmol) of the intermediate 51d was oxidized by the method of procedure 21c. 1.0 g (89%) of the product was obtained.

$^1$H-NMR(D$_6$-DMSO): δ=2.8(1H); 3.2(1H); 4.1(12H); 4.4 (1H); 7.0–8.0(16H); 8.8(1H) and 9.4(1H)ppm.

Example 53

(S)-4-Acetamido-2-(E-2-phenyl-1-ethenyl)-N-(3-phenylpropan-1-al-2-yl)benzamide

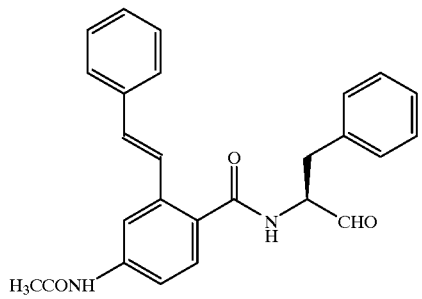

a) (S)-4-Acetamido-2-(E-2-phenyl-1-ethenyl)-N-(3-phenylpropan-1-ol-2-yl)benzamide 1 g (2.7 mmol) of (S)-4-amino-2(E-2-phenylethen-1-yl)-N-(3-phenylpropan-1-ol-2-yl)benzamide (intermediate 43f) was suspended in 50 ml of tetrahydrofuran and mixed with 0.25 ml (2.7 mmol) of acetic anhydride at 100° C. The mixture was stirred for 16 h. The reaction was then concentrated under reduced pressure and the residue was recrystallized from ethanol. 0.78 g (71%) of the product was obtained.

b) (S)-4-Acetamido-2-(E-2-phenyl-1-ethenyl)-N-(3-phenylpropan-1-al-2-yl)benzamide 0.65 g (1.6 mmol) of the intermediate 53a was oxidized with [lacuna] by the method of procedure 21c. 0.5 g (77%) of the product was obtained.

$^1$H-NMR(D$_6$-DMSO): δ=2.9(1H); 3.2(1H); 4.6(1H); 7–7.7(14H); 8.0(1H); 8.8(1H); 9.7(1H) and 10.1(1H) ppm.

Example 54

(S)-3-(8-Quinolinylsulfonamido)-N-(3-phenylpropan-1-al-2-yl)benzamide

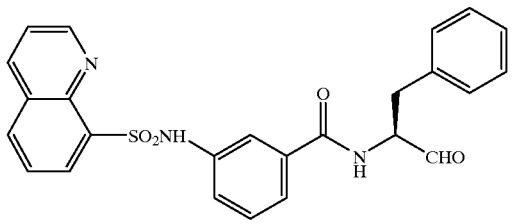

a) (S)-3-(8-Quinolinylsulfonamido)-N-(3-phenylpropan-1-ol-2-yl)benzamide 1.2 g (4.6 mmol) of (S)-4-amino-N-(3-phenylpropan-1-ol-2-yl)benzamide (intermediate 39b) were reacted with 8-guinolinesulfonyl chloride by the method of procedure 10a. 1 g of the product was obtained.

b) (S)-3-(8-Quinolinylsulfonamido)-N-(3-phenylpropan-1-al-2-yl)benzamide 0.9 g (1.95 mmol) of the intermediate 54a was oxidized with [lacuna] by the method of procedure 21c. 0.69 g (77%) of the product was obtained.

$^1$H-NMR(D$_6$-DMSO): δ=2.9(1H); 3.2(1H); 4.3(1H); 7.0–7.9(11H); 8.2(1H); 8.3(1H); 8.5(1H); 8.7(1H); 9.1(1H); 9.5(1H) and 10.2(1H) ppm.

Similarly to the abovementioned examples, further compounds according to the invention were prepared:

Example 55

(S)-4-(2-Fluoro-4-pyridylphenyl)amido-N-(3-phenylpropan-1-al-2-yl)benzamide

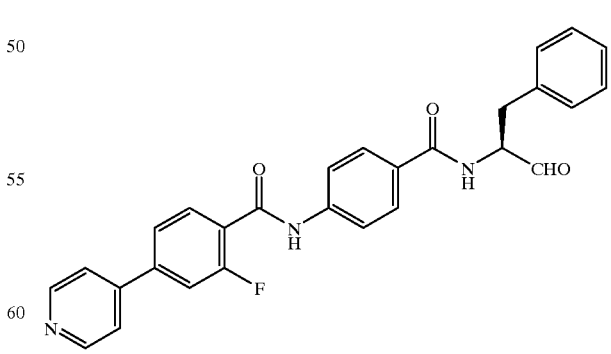

1H-NMR(CF$_3$COOD): δ=3.2(2H); 4.8(1H); 6.7(1H); 7.2–8.4(14H); 9.0(2H) and 11.8(1H) ppm.

Example 56

(S)-2-Fluoro-N-(3-phenylpropan-1-al-2-yl)-4-(4-pyridyl)benzamide

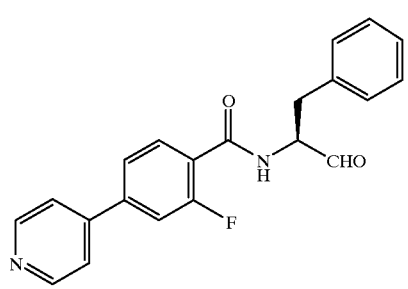

1H-NMR(CDCl₃): δ=3.3(2H); 4.95(1H); 7.2–7.6(10H); 8.2(1H); 8.7(1H) and 9.7(1H) ppm.

Example 57

N-(Butan-1-al-2-yl)-3-(8-quinolinyl)sulfonamidobenzamide

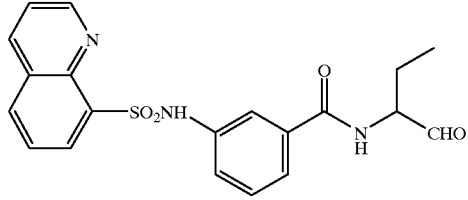

MS: m/e=441(M+).

Example 58

N-(Butan-1-al-2-yl)-4-(8-quinolinyl)sulfonamidobenzamide

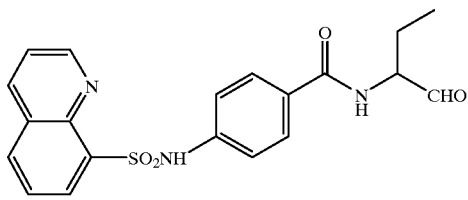

MS: m/e=397(M+).

Example 59

3-(8-Quinolinyl)sulfonamido-N-(pentan-1-al-2-yl)benzamide

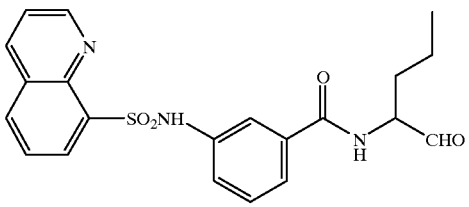

1H-NMR(CDCl₃): δ=1.3(3H); 1.75(2H); 2.0(2H); 4.7(1H); 6.55(1H); 7.2–7.7(6H); 8.0(1H); 8.3(2H); 8.7(broad); 9.1(1H) and 9.7(1H) ppm.

Example 60

4-(8-Quinolinyl)sulfonamido-N-(pentan-1-al-2-yl)benzamide

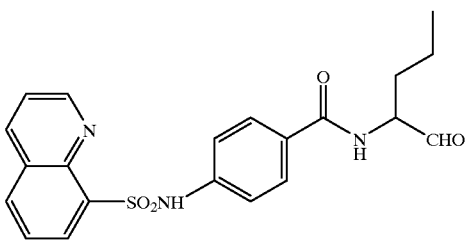

1H-NMR(D₆-DMSO): δ=1.2(3H); 1.4(2H); 1.75(2H); 4.1(1H); 7.15(2H); 7.5–7.8(4H); 8.3(1H); 8.4–8.7(3H); 9.1(1H); 9.3(1H) and 10.5(1H) ppm.

Example 61

N-(Pentan-1-al-2-yl)-2-(E-2-pyrid-2-ylethen-1-yl)benzamide hydrochloride

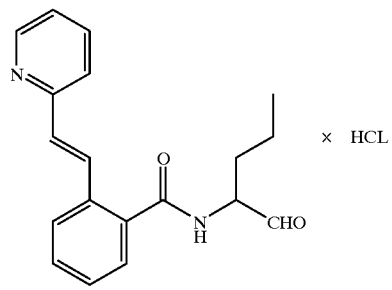

1H-NMR(D₆-DMSO): δ=0.9(3H); 1.4(2H); 1.6(1H); 1.8(1H); 4.4(1H); 7.3–8.5(9H); 8.7(1H); 8.9(1H) and 9.6(1H) ppm.

Example 62

(S)-N-(4-Methylpentan-1-al-2-yl)-2-(E-2-pyrid-2-ylethen-1-yl)benzamide hydrochloride

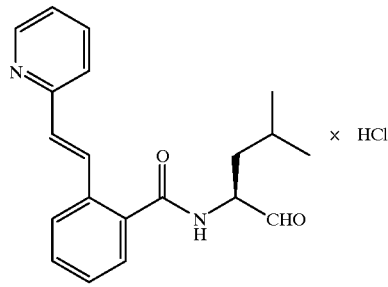

1H-NMR(D$_6$-DMSO): δ=0.9(3H); 1.5–1.9(3H); 4.4(1H); 7.4–8.2(9H); 8.4(1H); 8.8(1H); 9.0(1H) and 9.7(1H) ppm.

Beispiel 63

(S)-N-(4-Methylthiobutan-1-al-2-yl)-2-(E-2-pyrid-2-ylethen-1-yl)benzamide hydrochloride

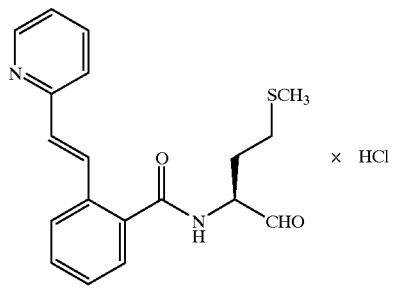

1H-NMR(D$_6$-DMSO): δ=2.0(1H); 2.3(1H); 2.55(3H); 2.7–3.0(2H); 4.4(1H); 7.5–8.5(10H); 8.8(1H); 9.2(1H); and 9.7(1H) ppm.

Example 64

N-(Butan-1-al-2-yl)-2-(E-2-pyrid-2-ylethen-1-yl)benzamide hydrochloride

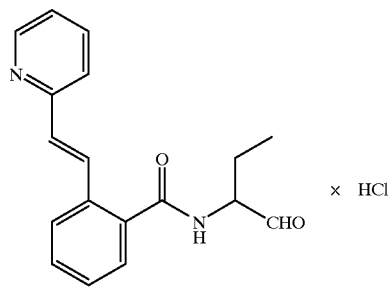

MS: m/e=294(M+).

Example 65

(S)-N-(3-Phenylprop-1-al-2-yl)-2-(E-2-pyrid-4-ylethen-1-yl)benzamide

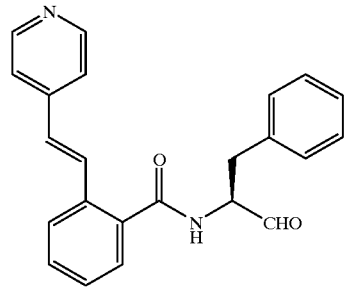

1H-NMR(CDCl$_3$): δ=3.3(2H); 5.05(1H); 6.55(1H); 6.9–7.8(13H); 8.5(2H) and 9.8(1H) ppm.

Example 66

(S)-N-(3-Phenylprop-1-al-2-yl)-4-(2-pyridyl)benzamide

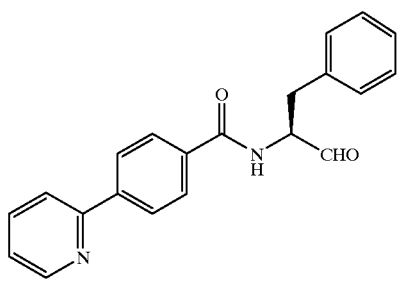

1H-NMR(D$_6$-DMSO): δ=3.0(1H); 3.3(1H); 4.5(1H); 7.1(1H); 7.25(3H); 7.35(1H); 7.9–8.2(6H); 8.7(1H); 9.0(1H) and 9.7(1H) ppm.

Example 67

(S)-N-(3-Phenylprop-1-al-2-yl)-2-(E-2-pyrid-2-ylethen-1-yl)benzamide

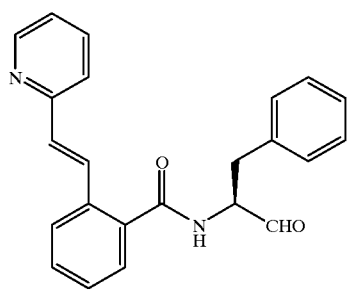

1H-NMR(CF$_3$COOD): δ=3.25(1H); 3.4(1H); 4.9(1H) and 7.2–8.8(16H) ppm.

Example 68

(S)-N-(3-Phenylprop-1-al-2-yl)-3-(3-pyridylsulfonamido)benzamide

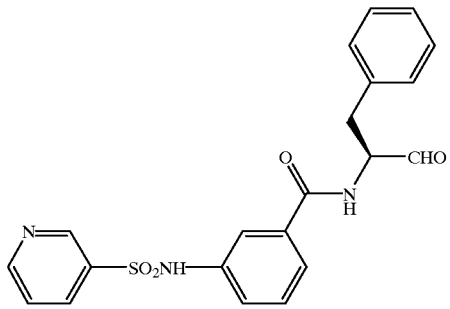

1H-NMR($D_6$-DMSO): δ=2.9(1H); 3.05(1H); 4.6(1H); 7.0–7.7(13H); 8.8(1H) and 10.0(1H) ppm.

Example 69

(S)-2-Methyl-N-(3-phenylprop-1-al-2-yl)-5-(3-pyridylsulfonamido)benzamide

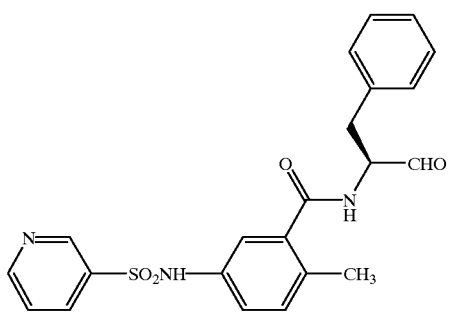

1H-NMR($D_6$-DMSO): δ=2.0(3H); 2.8(1H); 3.25(1H); 4.5(1H); 6.9–7.4(7H); 7.6(1H); 8.1(1H); 8.6–8.9(3H); 9.6(1H) and 10.5(1ppm.

Example 70

N-(Butan-1-al-2-yl)-2-(E-2-pyrid-2-ylethen-1-yl)benzamide hydrochloride

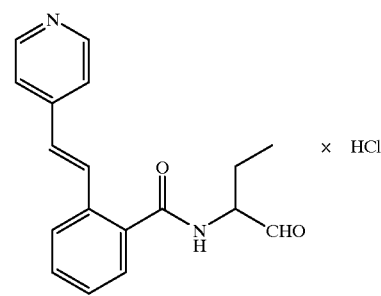

1H-NMR(CDCl$_3$): δ=1.0(3H); 1.8(1H); 2.1(1H); 4.8(1H); 6.5(1H); 6.9–7.9(6H), 8.5(2H) and 9.7(1H) ppm.

Example 71

(S)-4-Methanesulfonamido-2-(E-2-phenylethen-1-yl)-N-(3-phenylprop-1-al-2-yl)benzamide

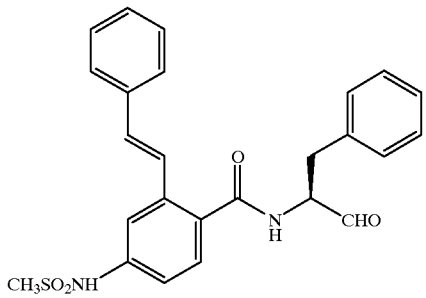

MS: m/e=448(M+).

Example 72

6-Methyl-N-(pentan-1-al-2-yl)-3-(3-pyridylsulfonamido)benzamide

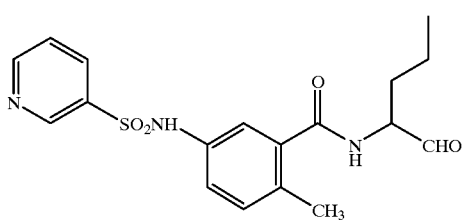

MS: m/e=375(M+).

Example 73

(S)-N-(3-Phenylprop-1-al-2-yl)-4-(4-pyridyl)benzamide

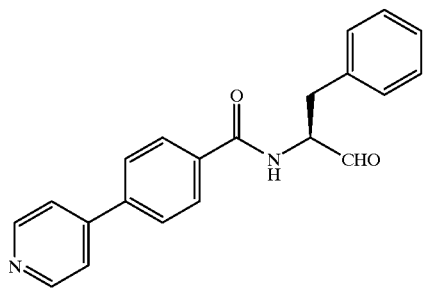

1H-NMR(CDCl$_3$): δ=3.35(2H); 5.O(1H); 6.8(1H); 7.2–7.9(11H); 8.7(2H) and 9.75(1H) ppm.

Example 74

N-(Pentan-1-al-2-yl)-2-(2-pyridylmethoxy)benzamide x methanesulfonic acid

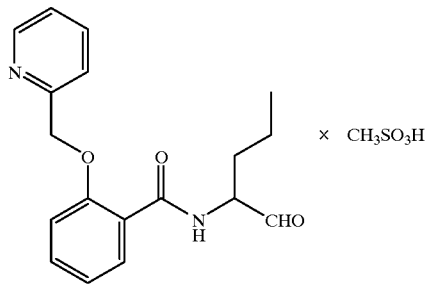

1H-NMR(CDCl$_3$): δ=0.9(3H); 1.3(2H); 1.7(1H); 1.9(1H); 4.7(1H); 5.3(2H); 7.0–7.9(6H); 8.2(1H); 8.6(1H); 8.9(1H); and 9.6(1H)ppm.

Example 75

N-(Pentan-1-al-2-yl)-2-(3-pyridylmethoxy)benzamide x methanesulfonic acid

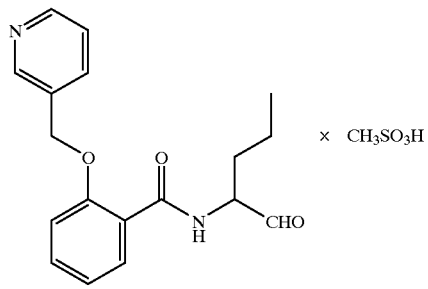

MS: m/e=312(M+).

Example 76

N-(Pentan-1-al-2-yl)-2-(E-2-pyrid-4-ylethen-1-yl)benzamide

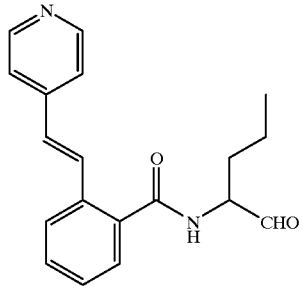

1H-NMR(D$_6$-DMSO): δ=1.0(3H); 1.4(2H),; 1.7(1H); 2.1(1H); 4.5(1H); 6.5(1H); 6.9–7.8(6H); 8.5(2H) and 9.7(1H) ppm.

Example 77

N-(Butan-1-al-2-yl)-2-(4-pyridylmethoxy)benzamide

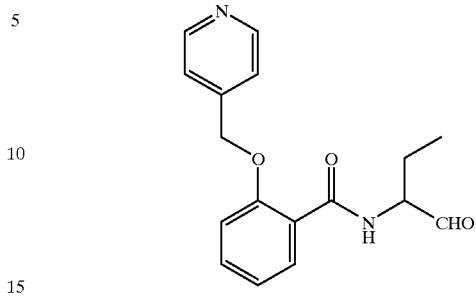

1H-NMR(CDCl$_3$): δ=0.8(3H); 1.7(1H); 2.0(1H); 4.7(1H); 5.25(2H); 7.0–7.6(5H); 8.2(1H); 8.3(1H); 8.6(1H) and 9.6(1H) ppm.

Example 78

N-(Hexan-1-al-2-yl)-2-(E-2-pyrid-2-ylethen-1-yl)benzamide hydrochloride

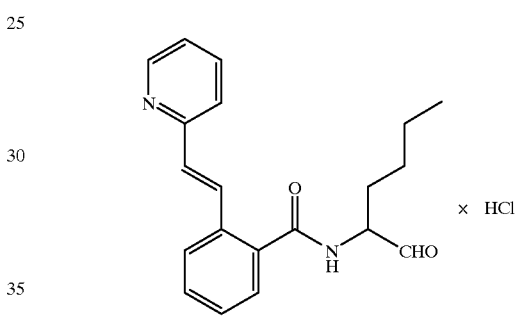

MS: m/e=322(M+).

Example 79

(S)-4-(Quinolin-2-yl)thiomethyl-N-(3-phenylpropan-1-al-2-yl)benzamide x fumaric acid

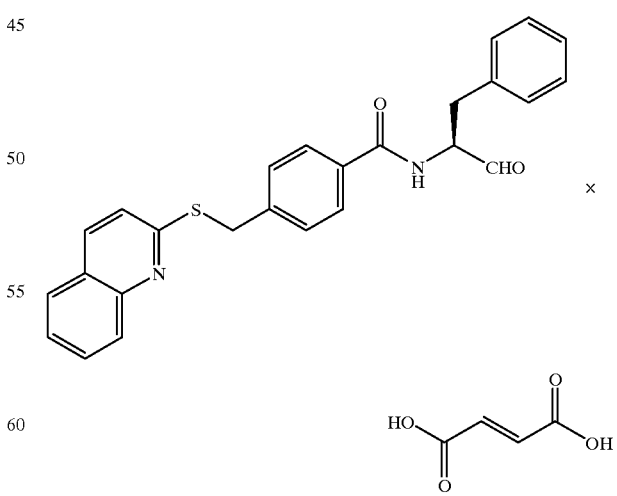

1H-NMR(D$_6$-DMSO): δ=2.8–3.0(1H); 3.2–3.4(1H); 4.5(1H); 4.6(2H); 6.6(2H); 7.0–8.2(13H); 8.8(1H) and 9.5(1H) ppm.

Example 80

4-(Quinolin-2-yl)thiomethyl-N-(3-pentan-1-al-2-yl)benzamide

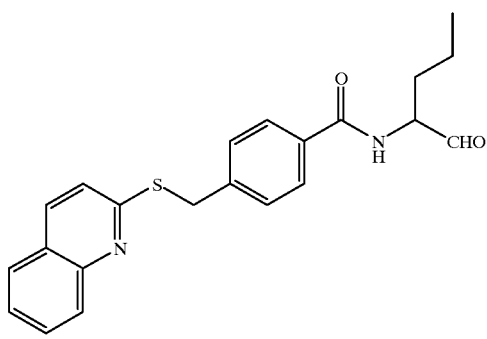

1H-NMR(D$_6$-DMSO): δ=0.9(3H); 1.2–1.9(4H); 4.2(1H); 4.7(2H); 7.3–8.2(10H); 8.8(1H) and 9.5(1H) ppm.

Example 81

2-(2-Quinolinylmethoxy)-N-(pentan-1-al-2-yl)benzamide

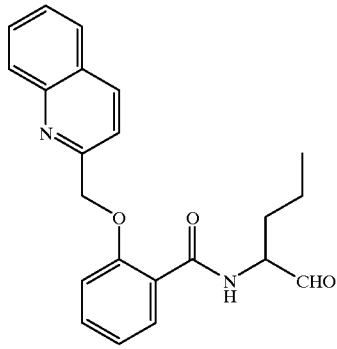

1H-NMR(D$_6$-DMSO): δ=0.7(3H); 1.2(2H); 1.3–1.8(2H); 4.3(1H); 5.5(2H); 7.0–8.0(9H); 8.4(1H); 8.8(1H) and 9.5(1H) ppm.

Example 82

N-(3-Pentan-1-al-2-yl)-4-(7-trifluoromethylquinolin-4-yl)thiomethylbenzamide

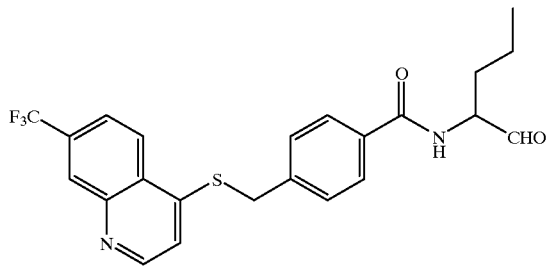

1H-NMR(D$_6$-DMSO): δ=0.9(3H); 1.2–1.9(4H); 4.2(1H); 4.6(2H); 7.6(3H); 7.9(3H); 8.3(2H); 8.8(2H) and 9.5(1H) ppm.

Example 83

(S)-4-(E-2-Isonicotinoyl-1-ethenyl)-N-(3-phenylpropan-1-al-2-yl)benzamide x fumaric acid

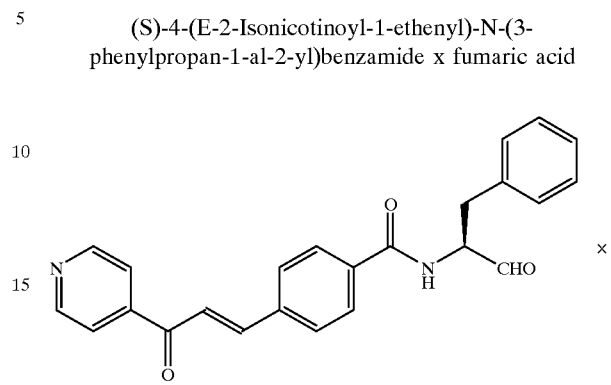

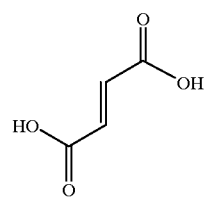

1H-NMR(D$_6$-DMSO): δ=2.7–3.0(2H); 4.2(1H); 6.7(2H); 7.25(5H); 7.75–8.1(8H); 8.3(2H); 8.8(2H); and 9.5(1H) ppm.

Example 84

(S)-4-Methoxy-3-(E-2-phenyl-1-ethenyl)amido-N-(3-phenylpropan-1-al-2-yl)benzamide

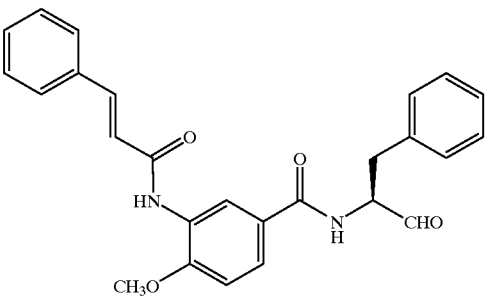

1H-NMR(D$_6$-DMSO): δ=2.9–3.1(1H); 3.25(1H); 4.0(3H); 4.5(1H); 7.1–7.7(14H); 8.6(1H); 8.8(1H); 9.5(1H) and 9.6(1H) ppm.

Example 85

4-(E-2-Isonicotinoyl-1-ethenyl)-N-(pentan-1-al-2-yl)benzamide

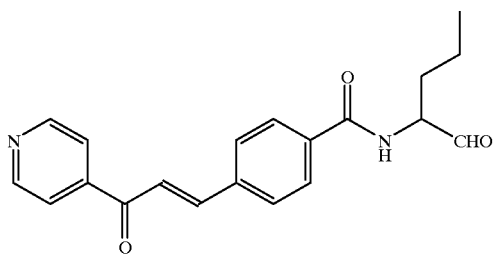

1H-NMR($D_6$-DMSO): δ=1.0(3H); 1.25–2.0(4H); 4.3 (1H); 7.9–8.2(8H); 8.9(2H); 9.0(1H) and 9.6(1H) ppm.

Example 86

(S)-4-Methoxy-3-(E-2-phenyl-1-ethenyl)amido-N-(pentan-1-al-2-yl)benzamide

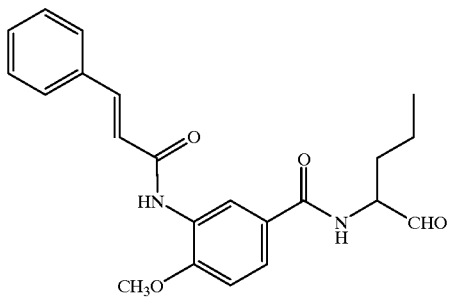

1H-NMR($D_6$-DMSO): δ=1.0(3H); 1.25–2.0(4H); 4.0 (3H); 4.25(1H); 7.1–7.75(10H); 8.6(1H); 8.75(1H) and 9.5 (1H) ppm.

We claim:
1. A benzamidoaldehyde of the formula I

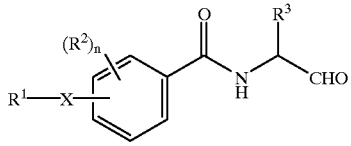

or a tautomeric or isomeric form or physiologically acceptable salt thereof, where:

$R^1$ is phenyl, naphthalene, quinoline, isoquinoline, tetrahydroquinoline, tetrahydroisoquinoline, pyridine, pyrimidine, pyrazine, pyridazine, quinazoline, quinoxaline, thiophene, benzothiophene, benzofuran, furan or indole, where the aromatic and heteroaromatic rings may be substituted by up to three radicals $R^4$, $R^2$ is hydrogen, chlorine, bromine, fluorine, phenyl with or without substitution by a $C_1$–$C_4$-hydrocarbon radical, —NHCO-$C_1$–$C_4$-alkyl, —NHCOPh, —NHCO-naphthyl, —NHSO$_2$-$C_{1-4}$-alkyl, —COO-$C_{1-4}$-alkyl, —CONH$_2$, COOH, —O-$C_{1-4}$-alkyl, —CO—NH-$C_{1-4}$-alkyl, NO$_2$ or NH$_2$, $R^3$ is a $C_1$–$C_6$-hydrocarbon radical, which may also carry a cyclopropyl, cyclobutyl, cyclopentyl, cyclohexyl, cycloheptyl, indolyl, phenyl, pyridine or naphthyl ring, it being possible for the rings in turn to be substituted by one or two radicals $R^4$, or is an —SCH$_3$ radical, $R^4$ is $C_1$–$C_4$-alkyl, —O-$C_1$–$C_4$-alkyl, OH, Cl, F, Br, I, CF$_3$, NO$_2$, NH$_2$, CN, COOH, COO-$C_1$–$C_4$-alkyl, —NHCO-$C_1$–$C_4$-alkyl, —NHCOPh, —NHSO$_2$-$C_1$–$C_4$-alkyl, —NHSO$_2$-Ph, —(CH$_2$)$_n$—NR$^5$R$^6$ (R$^5$ and R$^6$ are identical or different and are each hydrogen, $C_{1-4}$-alkyl or together are a ring), —SO$_2$-$C_1$–$C_4$-alkyl or —SO$_2$Ph, X is —(CH$_2$)$_m$—, —(CH$_2$)$_m$—O—(CH$_2$)$_o$—, —(CH$_2$)$_m$—S—(CH$_2$)$_o$—, —(CH$_2$)$_m$—SO—(CH$_2$)$_o$—, —(CH$_2$)$_m$—SO$_2$—(CH$_2$)$_o$—, —CH=CH—, —C≡C—, —CO—CH=CH—, —CH=CH—CO—, —(CH$_2$)$_m$—CO—(CH$_2$)$_o$—, —(CH$_2$)$_m$—NR$^5$CO—(CH$_2$)$_o$—, —(CH$_2$)$_m$—CONR$^5$—(CH$_2$)$_o$—, —(CH$_2$)$_m$—NHSO$_2$—(CH$_2$)$_o$—, —(CH$_2$)$_m$—SO$_2$NH—(CH$_2$)$_o$—, NH—CO—CH=CH—, —CH=CH—CO—NH— or n is the number 1 or 2, m is the number 0, 1, 2, 3 or 4, except that when X is —(CH$_2$)$_m$—, m is the number 1, 2, 3 or 4, and o is the nurmber 0, 1, 2, 3 or 4, except that when $R^1$ is phenyl and X is —O—(CH$_2$)$_o$—, o is the number 1, 2, 3 or 4.

2. A benzamide of the formula I as claimed in claim 1, where $R^2$ is hydrogen, $C_1$–$C_4$-alkyl, methoxy, fluorine, chlorine or bromine, $R^3$ is —CH$_2$-phenyl, —CH$_2$-cyclohexyl or —CH$_2$-indolyl, which may be substituted by $R^4$, and $R^1$, X, n, m and o are each as defined in claim 1.

3. A drug preparation for oral, parenteral or intraperitonal administration, comprising at least one benzamidoaldehyde of the formula I as claimed in claim 1.

4. A method of inhibiting cysteine protease in an animal comprising administering to said animal a cysteine protease inhibiting amount of a benzamidoaldehyde of the formula I as claimed in claim 1.

5. The method of claim 4 wherein the animal suffers from a neurodegenerative disorder and/or neuronal damage.

6. The method of claim 4 wherein the animal suffers from a neurodegenerative disorder and/or neuronal damage caused by ischemia, trauma or massive hemorrhages.

7. The method of claim 4 wherein the animal suffers from a cerebral vascular accident and/or craniocerebral trauma.

8. The method of claim 4 wherein the animal suffers from Alzheimer's disease or Huntingdon's disease.

9. The method of of claim 4 wherein the animal suffers from epilepsy.

10. The method of claim 4 wherein the animal suffers from damage to the heart after myocardial ischemia, damage to a kidney after renal ischemia, damage to a skeletal muscle, muscular dystrophy, damage caused by the proliferation of smooth muscles cells, coronal or cerebral vasospasm, a cataract of an eve and/or restenosis of a blood vessel after angioplasty.

11. The method of claim 4 wherein the animal suffers from a tumor and its metastasis comprising.

12. The method of claim 4 wherein the animal suffers from an increased interleukin-1 level.

13. The method of claim 4 wherein the animals suffers from an immunological disorder.

14. The method of claim 4 wherein the animal suffers from inflammation and/or a rheumatic disorder.

* * * * *

UNITED STATES PATENT AND TRADEMARK OFFICE
CERTIFICATE OF CORRECTION

PATENT NO. : 6,251,917 B1
DATED : June 26, 2001
INVENTOR(S) : Lubisch et al.

Page 1 of 1

It is certified that error appears in the above-identified patent and that said Letters Patent is hereby corrected as shown below:

<u>Title page,</u>
Item [87], PCT Pub. No.: "WO 93" should be -- WO 98 --;
PCT Pub. Date: "Apr. 6, 1998" should be -- June 4, 1998 --.

<u>Column 54, claim 1,</u>
Line 20, after "or" insert -- phenyl with or without substitution by a radical $R^2$, --.

<u>Column 54, claim 10,</u>
Line 57, "eve" should be -- eye --.

<u>Column 54, claim 11,</u>
Line 60, delete "comprising".

Signed and Sealed this

Nineteenth Day of March, 2002

Attest:

JAMES E. ROGAN
*Attesting Officer*  *Director of the United States Patent and Trademark Office*